(12) United States Patent
Payne et al.

(10) Patent No.: US 10,085,824 B2
(45) Date of Patent: Oct. 2, 2018

(54) SELF LIGATING ORTHODONTIC BRACKET

(71) Applicant: ORTHO ORGANIZERS, INC., Carlsbad, CA (US)

(72) Inventors: Mark A. Payne, Oceanside, CA (US); Colin Corey, Encinitas, CA (US)

(73) Assignee: ORTHO ORGANIZERS, INC., Carlsbad, CA (US)

( * ) Notice: Subject to any disclaimer, the term of this patent is extended or adjusted under 35 U.S.C. 154(b) by 0 days.

(21) Appl. No.: 15/081,574

(22) Filed: Mar. 25, 2016

(65) Prior Publication Data

US 2017/0119501 A1   May 4, 2017

Related U.S. Application Data

(60) Provisional application No. 62/249,110, filed on Oct. 30, 2015.

(51) Int. Cl.
| | |
|---|---|
| *A61C 3/00* | (2006.01) |
| *A61C 7/30* | (2006.01) |
| *A61C 7/28* | (2006.01) |

(52) U.S. Cl.
CPC .............. *A61C 7/30* (2013.01); *A61C 7/287* (2013.01)

(58) Field of Classification Search
CPC .... A61C 7/02; A61C 7/14; A61C 7/20; A61C 7/28; A61C 7/30; A61C 7/148; A61C 7/285; A61C 7/287
USPC ...................................................... 433/8–17
See application file for complete search history.

(56) References Cited

U.S. PATENT DOCUMENTS

| | | | |
|---|---|---|---|
| 4,712,999 A | 12/1987 | Rosenberg | |
| 4,846,681 A | 7/1989 | Mourany et al. | |
| 5,322,435 A | 6/1994 | Pletcher | |
| 5,466,151 A * | 11/1995 | Damon | A61C 7/146 |
| | | | 433/10 |
| 5,474,446 A | 12/1995 | Wildman et al. | |
| 5,618,176 A | 4/1997 | Andreiko et al. | |
| 5,630,715 A | 5/1997 | Voudouris | |
| 5,630,716 A | 5/1997 | Hanson | |

(Continued)

OTHER PUBLICATIONS

International Search Report, dated Feb. 2, 2017, 5 pages, from PCT/US2016/059197.

(Continued)

*Primary Examiner* — Yogesh Patel
*Assistant Examiner* — Gwen M Demosky
(74) *Attorney, Agent, or Firm* — Fulwider Patton LLP

(57) ABSTRACT

An orthodontic self-ligating bracket for orthodontic treatment of maloccluded teeth. The bracket includes a bracket body, a bracket door, and a spring mechanism retained by the bracket door. The bracket body has a base on the bottom side of the bracket body that is contoured to attach to a surface of a tooth, a bracket slot on the top side of the bracket body extending in a mesiodistal direction and configured to releasably retain an archwire, and a bracket groove on the top side of the bracket body extending in an occlusogingival direction towards the bracket slot. The spring mechanism includes one or more springs that are configured to contact the bracket door and the bracket body. The bracket door can thus be retained by and slidably engage the bracket body between an open position and a closed position. One or more additional active spring members may also be provided.

6 Claims, 13 Drawing Sheets

(56) References Cited

U.S. PATENT DOCUMENTS

| | | |
|---|---|---|
| 5,685,711 A | 11/1997 | Hanson |
| 5,711,666 A | 1/1998 | Hanson |
| 5,857,849 A | 1/1999 | Kurz |
| 5,906,486 A | 5/1999 | Hanson |
| 6,071,118 A | 6/2000 | Damon |
| 6,071,119 A | 6/2000 | Christoff et al. |
| 6,193,508 B1 | 2/2001 | Georgakis |
| 6,394,798 B1 | 5/2002 | Huff et al. |
| 6,485,299 B1 | 11/2002 | Wildman |
| 6,554,612 B2 | 4/2003 | Georgakis et al. |
| 6,582,226 B2 | 6/2003 | Jordan et al. |
| 6,632,088 B2 | 10/2003 | Voudouris |
| 6,709,268 B2 | 3/2004 | Pospisil et al. |
| 6,726,474 B2 | 4/2004 | Spencer |
| 6,957,957 B2 | 10/2005 | Pospisil |
| 7,094,052 B2 | 8/2006 | Abels et al. |
| 7,134,872 B2 | 11/2006 | Abels et al. |
| 7,134,873 B2 | 11/2006 | Miyaji et al. |
| 7,140,876 B2 | 11/2006 | Cinader et al. |
| 7,175,428 B2 | 2/2007 | Nicholson |
| 7,186,114 B2 | 3/2007 | Navarro et al. |
| 7,204,690 B2 | 4/2007 | Hanson |
| 7,210,927 B2 | 5/2007 | Abels et al. |
| 7,214,057 B2 | 5/2007 | Voudouris |
| 7,217,125 B2 | 5/2007 | Lai et al. |
| 7,247,019 B2 | 7/2007 | Abels et al. |
| 7,252,505 B2 | 8/2007 | Lai |
| 7,255,557 B2 | 8/2007 | Förster et al. |
| 7,267,545 B2 | 9/2007 | Oda |
| 7,306,457 B2 | 12/2007 | Vigolo |
| 7,335,020 B2 | 2/2008 | Castner et al. |
| 7,396,230 B2 | 7/2008 | Abels et al. |
| 7,416,408 B2 | 8/2008 | Farzin-Nia et al. |
| 7,419,375 B2 | 9/2008 | Farzin-Nia et al. |
| 7,611,352 B2 | 11/2009 | Abels et al. |
| 7,611,353 B2 | 11/2009 | Sommer |
| 7,621,743 B2 | 11/2009 | Bathen et al. |
| 7,677,887 B2 | 3/2010 | Nicholson |
| 7,686,613 B2 | 3/2010 | Pospisil et al. |
| 7,704,072 B2 | 4/2010 | Damon |
| 7,717,706 B2 | 5/2010 | Förster et al. |
| 7,780,443 B2 | 8/2010 | Hagelganz et al. |
| 7,785,101 B2 | 8/2010 | Förster et al. |
| 7,828,549 B1 | 11/2010 | Wildman |
| 7,845,940 B2 | 12/2010 | Minium |
| 7,878,802 B2 | 2/2011 | Hagelganz et al. |
| 7,963,767 B2 | 6/2011 | Lewis et al. |
| 8,029,275 B2 | 10/2011 | Kesling |
| 8,029,276 B1 | 10/2011 | Lokar |
| 8,033,824 B2 | 10/2011 | Oda et al. |
| 8,038,438 B2 | 10/2011 | Ruiz Diaz et al. |
| D648,030 S | 11/2011 | Bryant et al. |
| 8,113,827 B2 | 2/2012 | Farzin-Nia et al. |
| 8,113,828 B1 | 2/2012 | Greenfield |
| 8,162,660 B2 | 4/2012 | Rudman |
| 8,220,195 B2 | 7/2012 | Maijer et al. |
| 8,246,347 B2 | 8/2012 | Oda |
| 8,246,348 B2 | 8/2012 | Heiser |
| 8,246,349 B2 | 8/2012 | Scommegna et al. |
| 8,251,696 B2 | 8/2012 | Rodriguez et al. |
| 8,282,392 B2 | 10/2012 | Hilliard |
| 8,297,970 B2 | 10/2012 | Kanomi et al. |
| 8,371,846 B2 | 2/2013 | Kishi |
| 8,414,292 B2 | 4/2013 | Lopes |
| 8,469,704 B2 | 6/2013 | Oda et al. |
| 8,568,139 B2 | 10/2013 | Roncone |
| 8,573,971 B2 | 11/2013 | Stevens |
| 8,585,398 B2 | 11/2013 | Yeh et al. |
| 8,636,507 B2 | 1/2014 | Voudouris |
| 8,714,972 B2 | 5/2014 | Eichenberg |
| 8,714,973 B2 | 5/2014 | Zucchi et al. |
| 8,827,698 B2 | 9/2014 | Lai et al. |
| 8,932,053 B2 | 1/2015 | Curiel et al. |
| 8,961,172 B2 | 2/2015 | Dupray et al. |
| 8,979,528 B2 | 3/2015 | Macchi et al. |
| 9,004,916 B2 | 4/2015 | Ruiz-Vela et al. |
| 9,089,386 B2 | 7/2015 | Hagelganz et al. |
| 9,226,803 B2 | 1/2016 | Cosse et al. |
| 9,241,775 B2 | 1/2016 | Romano et al. |
| 2001/0005574 A1 | 6/2001 | Manemann et al. |
| 2002/0110771 A1 | 8/2002 | Abels et al. |
| 2005/0239012 A1* | 10/2005 | Bathen ............... A61C 7/287 433/10 |
| 2006/0228662 A1 | 10/2006 | Lokar et al. |
| 2006/0263737 A1 | 11/2006 | Oda |
| 2006/0269895 A1* | 11/2006 | Voudouris ............ A61C 7/02 433/10 |
| 2007/0082315 A1 | 4/2007 | Sabater |
| 2007/0178422 A1 | 8/2007 | Voudouris |
| 2009/0004617 A1 | 1/2009 | Oda et al. |
| 2009/0298003 A1 | 12/2009 | Wei et al. |
| 2010/0129765 A1 | 5/2010 | Mohr et al. |
| 2010/0178629 A1* | 7/2010 | Oda ..................... A61C 7/125 433/14 |
| 2011/0076633 A1* | 3/2011 | Bryant ................. A61C 7/287 433/11 |
| 2011/0086323 A1 | 4/2011 | Wessinger |
| 2012/0058442 A1 | 3/2012 | Oda et al. |
| 2012/0135364 A1 | 5/2012 | Tuneberg et al. |
| 2013/0045455 A1 | 2/2013 | Farzin-Nia |
| 2013/0224676 A1* | 8/2013 | Alauddin ............. C22F 1/183 433/3 |
| 2013/0285268 A1 | 10/2013 | Munoz et al. |
| 2014/0038120 A1 | 2/2014 | Lin et al. |
| 2014/0065566 A1 | 3/2014 | Lai et al. |
| 2014/0127638 A1* | 5/2014 | Huang ................. A61C 7/287 433/11 |
| 2014/0134563 A1 | 5/2014 | Voudouris |
| 2014/0141383 A1* | 5/2014 | Hagelganz ........... A61C 7/287 433/9 |
| 2014/0178831 A1 | 6/2014 | Förster et al. |
| 2014/0199648 A1 | 7/2014 | Lopes |
| 2014/0212828 A1 | 7/2014 | Falcone et al. |
| 2014/0272752 A1 | 9/2014 | Huang |
| 2014/0272753 A1* | 9/2014 | Sommer ............... A61C 7/30 433/11 |
| 2014/0295369 A1 | 10/2014 | Nóbrega et al. |
| 2014/0308622 A1 | 10/2014 | Voudouris |
| 2014/0370454 A1 | 12/2014 | Rudman |
| 2015/0157422 A1 | 6/2015 | Cosse et al. |
| 2015/0173859 A1 | 6/2015 | Lin et al. |
| 2015/0173860 A1 | 6/2015 | Oda |
| 2015/0182304 A1 | 7/2015 | Gualano |
| 2015/0182307 A1 | 7/2015 | Yick |
| 2015/0202026 A1 | 7/2015 | Voudouris |
| 2015/0209121 A1 | 7/2015 | Ruiz-Vela et al. |
| 2015/0216629 A1 | 8/2015 | Voudouris |
| 2015/0223913 A1* | 8/2015 | Yick .................... A61C 7/287 433/10 |
| 2015/0230887 A1 | 8/2015 | Damon et al. |
| 2015/0265377 A1 | 9/2015 | Wu et al. |
| 2015/0342707 A1 | 12/2015 | Fernandez San Pablo |
| 2015/0351873 A1 | 12/2015 | Sabilla |
| 2016/0030139 A1 | 2/2016 | Braun |
| 2016/0038258 A1 | 2/2016 | Sabilla et al. |
| 2016/0045286 A1 | 2/2016 | Damon et al. |
| 2017/0119500 A1* | 5/2017 | Ruiz-Vela ............ A61C 7/287 |

OTHER PUBLICATIONS

International Search Report and Written Opinion, dated Nov. 6, 2017, 7 pages, from PCT/US2017/050741.

* cited by examiner

SELF LIGATING ORTHODONTIC BRACKET

CROSS-REFERENCES TO RELATED APPLICATIONS

This application claims priority from provisional U.S. Application No. 62/249,110, filed Oct. 30, 2015, which is incorporated by reference in its entirety.

BACKGROUND

The present invention relates generally to orthodontic brackets for providing orthodontic treatment of maloccluded teeth, and more specifically relates to a self-ligating orthodontic bracket with a sliding door for releasably retaining an archwire in a bracket slot.

Orthodontic brackets or braces are a very popular method of treating misaligned or maloccluded teeth. Traditionally, brackets are bonded to the labial or possibly lingual surfaces of a patient's teeth, and an archwire is placed in the slot of each bracket to guide movement of the teeth. Brackets are generally pre-adjusted to have built-in prescriptions of torque, tip, and in-out which are optimized for average cases of tooth movement. For instance, a bracket may be angled with respect to an occlusal plane (i.e. the bracket has a "tip angle"), depending on the tooth on which the bracket is to be placed. A ligature or ligating module, typically an elastomeric band such as a rubber band, is placed around the tie wings of a bracket to hold the archwire in place. However, ligatures typically cause friction on the wire during movement, resulting in a relatively slow treatment process, and they tend to attract plaque and trap food particles, a common cause of tooth decay or infection. As a result, the use of self-ligating orthodontic brackets has steadily become a prevalent alternative solution to malocclusion treatment.

A self-ligating orthodontic bracket does not require a ligature to hold the archwire in place. Rather, the bracket uses a clip or slide which opens and closes to releasably retain the archwire in the bracket slot. Thus, friction on wire movement is reduced compared to conventional brackets, resulting in potentially faster treatment time. An example of a conventional self-ligating bracket includes a base for attachment to a tooth surface, an archwire slot sized for receiving an archwire, a channel formed upon the base and transversely oriented to the archwire slot, and a sliding member slidably retained in the channel and closeable over the archwire slot. The sides of the bracket are crimped to securely retain the sliding member. Another type of self-ligating bracket includes a flexible pin to secure the sliding member in the closed position. However, these types of self-ligating brackets require additional processes or additives for securing the sliding member to the bracket, thus adding an additional layer of manufacturing complexity and increased cost.

Additionally, errors made while coining, bending, or crimping the sides of the bracket to retain the sliding member are typically irreversible without damaging the bracket, thus potentially resulting in significantly higher expenditures. For example, too much compression applied to the sides of the bracket may preclude the sliding member from moving, thus requiring the brackets to be discarded. Moreover, too little compression applied to the sides of the bracket may cause the sliding member to accidentally disengage from the bracket during use, resulting in patient and physician dissatisfaction and possible bracket recalls.

Hence, it is desirable to facilitate the assembly process by providing a self-ligating bracket that does not require crimping, bending, coining, fastening, or gluing the sliding member to the bracket. Additionally, it is desirable to provide a self-ligating bracket that is easy to manufacture and assemble, that is cost-effective, that requires no adhesives nor additives to assemble the sliding member to the bracket, and that reduces plaque buildup through minimal empty space in the bracket. It is further desirable to provide a self-ligating orthodontic bracket that can passively or actively express the bracket's prescription by providing for the sliding member to fully enclose the archwire in the bracket slot. Moreover, it is desirable to provide metallic and aesthetic self-ligating brackets with lower profiles, improved patient comfort, ease of manufacture, improved door operation, and improved visual orthodontic references. The present invention meets these and other needs.

SUMMARY OF THE INVENTION

The self-ligating orthodontic bracket according to the present invention provides one or more benefits and advantages not previously offered by the prior art, including but not limited to, a self-ligating bracket that does not require crimping, bending, coining, fastening, or gluing the sliding member or bracket door to the bracket. The self-ligating bracket may be passive or active, and it incorporates a spring mechanism that is borne by the bracket door. In a preferred embodiment, the spring mechanism biases or propels the bracket door between an opened position and a closed position, allows for easy assembly of the bracket door to the bracket body while preventing disassembly, and may be cost-effectively used for any self-ligating bracket regardless of bracket prescription.

Accordingly, there is provided an orthodontic self-ligating bracket for orthodontic treatment of maloccluded teeth that includes a bracket body having a bottom, lingual side and a top, labial side, a bracket door having a bottom, lingual side and a top, labial side, and a spring mechanism that includes one or more springs configured to contact and be retained by the bracket door. The bracket body has a base on the bottom side of the bracket body that is contoured to attach to a surface of a tooth, a bracket slot on the top side of the bracket body extending in a mesiodistal direction and configured to releasably retain an archwire, and a bracket groove on the top side of the bracket body extending in an occlusogingival direction. Preferably, the bracket body has one or more first depressions and one or more second depressions that are sized to engage or receive the one or more springs.

The bracket door slidably engages the bracket groove between an open position, in which the bracket slot is exposed to allow for placement and removal of the archwire, and a closed position, in which the bracket slot is enclosed to securely retain the archwire. In a preferred embodiment, the bracket door is slidably movable and is propelled into the open position upon application of a force to the door such that the one or more springs slide into the one or more first depressions, and the bracket door is slidably movable and is propelled into the closed position upon application of a force to the door such that the one or more springs slide into the one or more second depressions.

In a preferred embodiment of the present invention, the one or more springs include a mesial spring and a distal spring, each of which is configured to contact the bracket door and the mesial or distal side of the bracket groove, respectively. The bracket body includes a mesial recess on a mesial side of the bracket groove having a mesial first depression and a mesial second depression, and a distal recess on a distal side of the bracket groove having a distal first depression and a distal second depression. In this embodiment, the bracket door is slidably movable and is propelled into the open position upon application of a force to the door such that the mesial spring slides into the mesial first depression and the distal spring slides into the distal first depression. Similarly, the bracket door is slidably movable and is propelled into the closed position upon application of a force to the door such that the mesial spring slides into the mesial second depression and the distal spring slides into the distal second depression.

In a preferred aspect, the mesial first depression and the mesial second depression taper off towards each other at a first midpoint, and the distal first recess and the distal second recess taper off towards each other at a second midpoint. In this way, the first midpoint and the second midpoint define the positions where the bracket door propels from the open position towards the closed position, and vice-versa.

Preferably, the mesial spring and the distal spring each have a first end, an intermediate segment, and a second end. Each spring's first end is configured to contact the bracket door, and each spring's second end is configured to contact the bracket body. Additionally, each spring's intermediate segment is preferably shaped to maximize the running length of the spring and distribute stresses caused by movement of the bracket door, for example in a U-shaped configuration. Moreover, each spring's intermediate segment is configured to wrap around a surface of the bracket door.

According to another presently preferred aspect, the mesial spring and the distal spring are configured to contact the bracket door and the bracket body such that the first end and the second end of each spring are positioned on different planes, and such that the intermediate segment of each spring is positioned on another plane angled with respect to the planes on which the first end and the second end of each spring are aligned. In one aspect, the planes on which the first end and the second end of each spring are aligned are orthogonal planes. In an alternative aspect, the planes on which the first end and the second end of each spring are aligned are parallel planes.

In this preferred embodiment, the bracket door includes a receiving feature that is sized to engage or receive the one or more springs. According to a presently preferred aspect, the receiving feature is on the bottom side of the bracket door and includes a mesial cavity having a trailing mesial groove and a distal cavity having a trailing distal groove. The mesial cavity is configured to receive the first end of the mesial spring such that the intermediate segment of the mesial spring travels along the trailing mesial groove. Moreover, the distal cavity is configured to receive the first end of the distal spring such that the intermediate segment of the distal spring travels along the trailing distal groove. In an alternative preferred aspect, the receiving feature includes ledges in lieu of a mesial cavity and a distal cavity which are configured to receive the first ends of the mesial and distal springs.

The receiving feature preferably includes one or more recesses on a surface of the bracket door, for example, a curved spring recess on both the mesial side and the distal side of the bracket door. The surface may be external or internal to the bracket door. Moreover, each intermediate segment is configured to wrap around the surface of the bracket door within each curved spring recess.

In other preferred aspects, the bracket door includes relief areas within which the second end of the mesial spring and the second end of the distal spring deflect when the bracket door is slidably engaged with the bracket groove and moved between the open position and the closed position. Moreover, the bracket groove includes tapered sides that are configured to contact the mesial spring and the distal spring as the bracket door is slidably inserted into the bracket groove. In some aspects, the bracket may be oriented at a tip angle relative to an occlusal plane, and the mesial spring and the distal spring are positioned to accommodate the tip angle.

The self-ligating orthodontic bracket of the present invention may be passive or active. In the active version of the preferred embodiment described above, the bracket includes one or more active springs that each include a first portion and a second portion. Preferably, the first portion of each active spring is insertable into and retained by the bracket door, and the second portion of each active spring contacts the archwire in the bracket slot when the bracket door is in the closed position. Alternatively, the active spring is a tang that is integrally borne by and extending from the bracket door.

In a preferred aspect, the bracket door retains the one or more active springs using a receiving feature on the bottom side of the bracket door that includes a recess and a channel. The recess receives the first portion of the one or more active springs, and the channel is sized to receive the second portion of the one or more active springs as it engages or contacts the archwire. In another presently preferred aspect, the bracket door includes a relief area that is connected to the channel.

Various other preferred aspects are contemplated within the scope of the preferred embodiments described above. For example, in one preferred aspect, the preferred embodiments of the present invention can be passive or active brackets as previously described. In another preferred aspect, the base of the bracket body is dual compound contoured to engage a surface of a molar tooth. In another preferred aspect, the base of the bracket may be smooth, or it may have a bonding system. For example, the bonding system of the base may include pylons or mesh. Alternatively, the base may have a smooth surface with small shards of ceramic as the bracket's bonding system.

According to another presently preferred aspect, the bracket has a predetermined prescription including tip angle and torque. In embodiments where a plurality of springs are used, the springs are preferably mirror images of each other and therefore allow the orthodontic self-ligating bracket to operate for any predetermined bracket prescription, regardless of tip angle and torque.

According to yet another presently preferred aspect, the top side of the bracket body includes a tool depression adjacent to the bracket slot that is configured to accept a tool for opening the bracket door when the bracket door is in the closed position. According to another presently preferred aspect, the bracket body includes curved tie wing grooves for optional placement of ligatures on the gingival side of the bracket body and on the occlusal side of the bracket body. According to another presently preferred aspect, the top side of the bracket body and the bracket door includes an area or groove for applying a visual orthodontic reference.

According to a further presently preferred aspect, the outside edges of the bracket slot are rounded to prevent notching of the archwire. In another preferred aspect, the bracket slot includes a fluted inlet to facilitate insertion of the archwire into the bracket slot. In another presently preferred aspect, the top side of the bracket door is rounded to improve patient comfort. According to another presently preferred aspect, the one or more springs are round wire springs. According to another presently preferred aspect, the bracket door, the bracket body, and the one or more springs are engaged to leave minimal empty space for plaque growth or calcification. According to another presently preferred aspect, the bracket door and bracket groove are shaped in the form of a male and female dovetail, respectively.

Other features and advantages of the present invention will become more apparent from the following detailed description of the preferred embodiments in conjunction with the accompanying drawings, which illustrate, by way of example, the operation of the invention.

DETAILED DESCRIPTION OF THE PREFERRED EMBODIMENTS

The present invention provides for a self-ligating orthodontic bracket that is easier to assemble and more cost-effective than conventional self-ligating orthodontic brackets. The present invention does not require crimping, bending, coining, fastening, or gluing a clip or slide to a bracket, but rather uses a force giving mechanism, preferably a spring mechanism, to assemble the slide to the bracket. The present invention also requires no adhesives or additives, helps to reduce plaque buildup by having minimal empty space in the bracket, and provides for metallic and aesthetic self-ligating brackets with lower profiles, increased patient comfort, easier manufacturing, improved opening and closing forces and mechanisms, and improved visual cues for a doctor.

Figure 1:
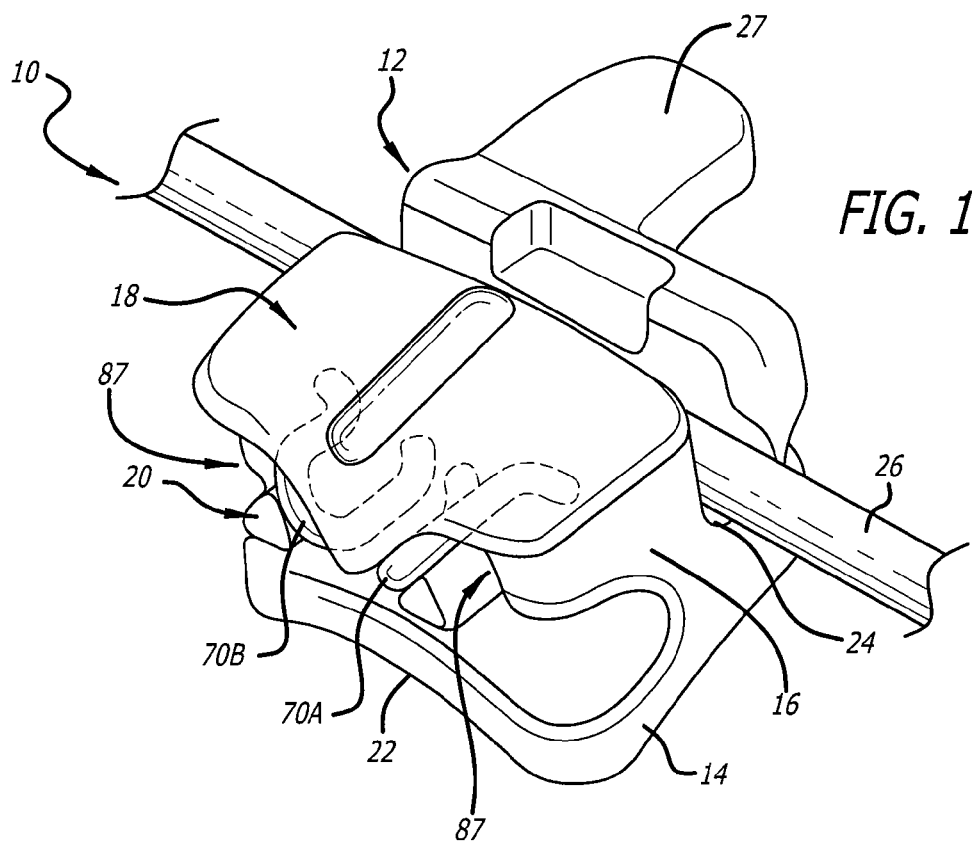
FIG. 1 is a perspective view of a self-ligating orthodontic bracket having a bracket body, a bracket door, and one or more springs according to a preferred embodiment of the present invention.

FIG. 1 illustrates a self-ligating orthodontic bracket 10 according to an embodiment of the present invention. The self-ligating bracket includes a bracket body 12 having a lingual side or bottom side 14 and a labial side or top side 16, a bracket door or slide 18 which slidably engages with the bracket body, and a spring mechanism 20 including one or more springs (70A and 70B) that engage the bracket body and the bracket door. In one preferred aspect, the spring mechanism is constantly under tension as it engages the bracket body and the bracket door. In an alternative preferred aspect, the spring mechanism is in a resting, substantially tensionless state when it engages the bracket body and the bracket door. The spring mechanism is preferably not visible to a user when viewing the top side or labial surface of the self-ligating bracket.

The bottom side of the bracket body has a base 22 which is compound contoured to engage a surface of a tooth, and an archwire slot or bracket slot 24 is positioned on the top side of the bracket body. The bracket slot extends in a mesiodistal direction and is sized to releasably retain an archwire 26. Preferably, the outside edges of the bracket slot are rounded to help prevent archwire notching during orthodontic treatment, thus reducing the risk of fray or damage caused by movement of the archwire within the bracket slot. The bracket body and bracket door are preferably created using injection molded components, and they can be manufactured from metallic, ceramic, plastic, or other types of material. Optionally, the self-ligating bracket 10 includes a hook 27 that is shaped to facilitate attachment of an elastomeric, such as a ligature, onto the hook, without coming into contact with the gingiva. The shape of the hook may vary depending on the material used for the self-ligating bracket to provide increased strength for the bracket. The individual components of the self-ligating orthodontic bracket and how they interoperate are discussed in reference to the following Figures.

Figure 2:
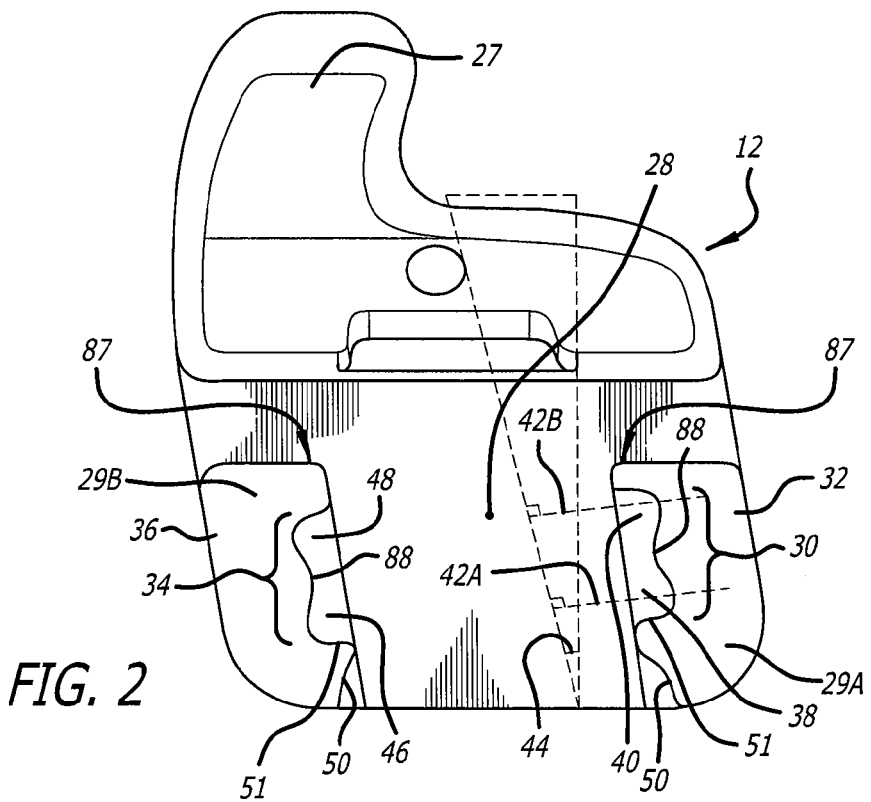
FIG. 2 is a top plan view of the bracket body of the self-ligating orthodontic bracket depicted in FIG. 1.

Referring to FIG. 2, the top side of the bracket body includes a bracket groove 28, a mesial surface 29A, and a distal surface 29B. The bracket groove 28 extends in an occlusogingival direction and includes opposing side slots (87) which guide movement of the bracket door along the bracket groove. The mesial surface 29A and distal surface 29B of the bracket body further support movement of the bracket door along the bracket groove. In one preferred aspect, the bracket groove ultimately connects with the bracket slot, as illustrated in FIG. 2. Alternatively, a wall (not shown in the Figures) may separate the bracket groove from the bracket slot.

The bracket body preferably includes one or more recesses sized to receive or engage the one or more springs of the spring mechanism. The one or more recesses may be on the sides of the bracket body, as exemplarily depicted in FIG. 2. Alternatively, the one or more recesses may be positioned anywhere within the bracket groove. In the exemplary embodiment depicted in FIG. 2, a mesial recess 30 is positioned on a mesial side 32 of the bracket body adjacent to the bracket groove, and a distal recess 34 is positioned on a distal side 36 of the bracket body adjacent to the bracket groove. The mesial recess includes a mesial first depression 38 positioned away from the bracket slot and a mesial second depression 40 positioned towards the bracket slot that both respectively have center lines 42A and 42B that are preferably oriented perpendicular to the bracket's tip angle 44. Similarly, the distal recess includes a distal first depression 46 positioned away from the bracket slot and a distal second depression 48 positioned towards the bracket slot also both respectively having center lines that are preferably oriented perpendicular to the bracket's tip angle. In an alternative embodiment (not shown in the Figures), the recess may be positioned within the bracket groove, for example, in the center of the bracket groove, and may include a first depression positioned away from the bracket slot and a second depression positioned towards the bracket slot.

The one or more depressions are sized to engage the spring mechanism such that the bracket door can alternate or switch between an open position, in which the bracket slot is exposed such that a user can remove or place an archwire, and a closed position, in which the bracket slot is enclosed such that the archwire is securely retained in the bracket slot. For example, in the exemplary embodiment depicted in FIGS. 1 and 2, the bracket door is slidably movable into the open position upon application of a force to the door such that the spring mechanism slides into the mesial first depression and the distal first depression and propels or biases the door open. Similarly, the bracket door is slidably movable into the closed position upon application of a force to the door such that the spring mechanism slides into the mesial second depression and the distal second depression and propels or biases the door closed. Preferably, the distance between the center lines of the mesial first depression and the mesial second depression (the distance between 42A and 42B) and the distance between the center lines of the distal first depression and the distal second depression are preferably sized to allow for the open position of the bracket door to sufficiently clear the bracket slot.

In a preferred embodiment, the self-ligating orthodontic bracket may be preassembled with the bracket door operatively engaged to the bracket body. Alternatively, the bracket door may be a separate component, in which case the bracket door can be easily assembled as subsequently described to engage with the bracket body. The bracket body includes tapered sides 50 positioned on both the mesial side and distal side of the bracket body which taper towards the bracket groove. These tapered sides engage the spring mechanism as the bracket door is slidably pushed towards the mesial first depression 38 and the distal first depression 46, allowing for easy assembly of the bracket door to the bracket body. Moreover, depressions 38 and 46 each include side walls 51 that are preferably, cooperatively angled to retain the spring mechanism and prevent accidental disassembly of the bracket door from the bracket body.

Figure 3A:
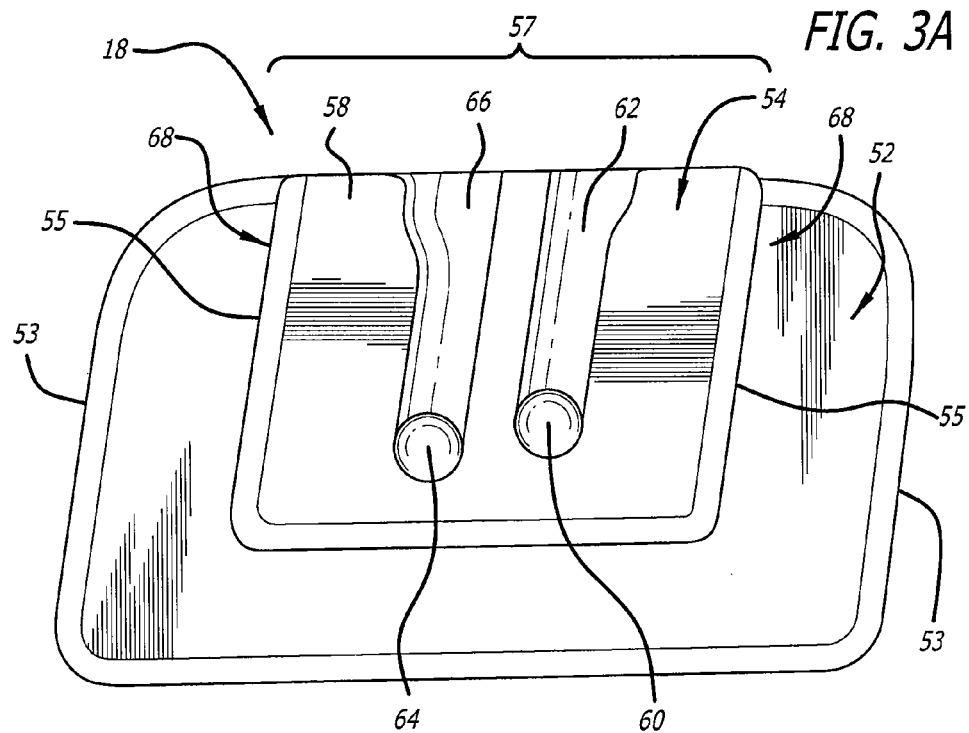
FIG. 3A is a bottom plan view of the bracket door of the self-ligating orthodontic bracket depicted in FIG. 1.
Figure 3B:
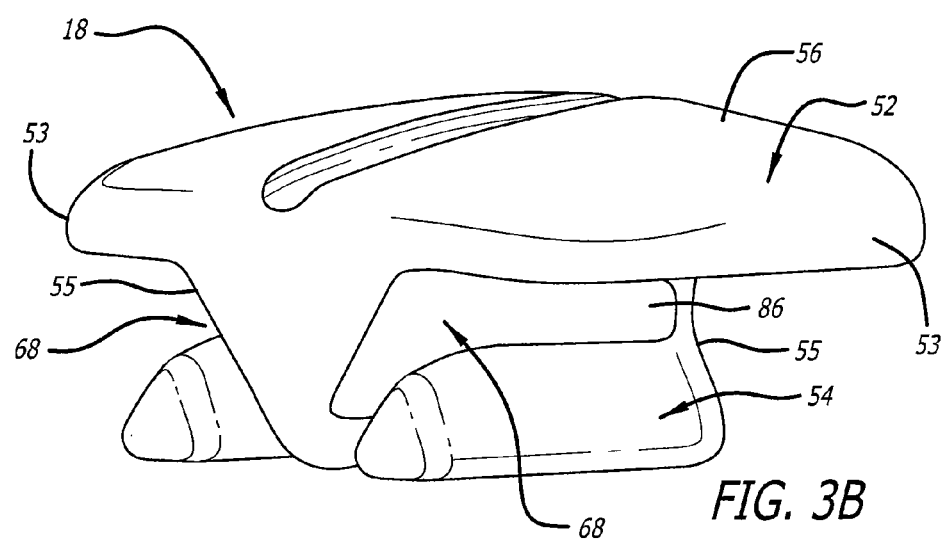
FIG. 3B is a perspective view of the bracket door depicted in FIG. 3A.

Referring to FIGS. 3A and 3B, the bracket door includes a door head 52 having opposing side edges 53, and a door base 54 having preferably curved, opposing side edges 55. The top side 56 of the door head is preferably rounded to improve patient comfort. Preferably, the bracket door extends throughout the entire width of the bracket in a continuous surface without crevices or jagged edges, thus preventing plaque and further improving patient comfort. The bracket door also preferably extends the entire width of the archwire slot, allowing for better expression of the bracket prescription.

In a preferred aspect, the spring mechanism includes one or more springs, and the bracket door includes a receiving feature 57 sized to engage the one or more springs. The receiving feature operates to lock and implement the spring mechanism. In the preferred embodiment depicted in FIG. 3A, in which the spring mechanism includes two springs, the receiving feature 57 is on the bottom side 58 of the door base and includes two cavities and two grooves, namely a mesial cavity 60 having a trailing mesial groove 62, and a distal cavity 64 having a trailing distal groove 66. In an alternative exemplary embodiment (not shown in the Figures), the spring mechanism may include only one spring, and the receiving feature on the bottom side of the door base may include only one cavity and groove, for example a center cavity having a trailing center groove. It should be noted that although the Figures depict the receiving feature on the bottom side of the door base, the receiving feature is not so limited; for example, the receiving feature may be located at a different position inside or on a surface of the bracket door.

Furthermore, the receiving feature 57 preferably includes one or more spring recesses 68 that curve around a surface of the door base and that are sized to engage the spring mechanism. For example, in the preferred embodiment illustrated in FIG. 3B, the spring recesses 68 curve around an external surface of both a mesial side and a distal side of the door base. Alternatively, the spring recess may curve around an internal surface of the door base, for example, within a trailing center groove. Various other configurations for the receiving feature may be contemplated by a person of ordinary skill to engage the spring mechanism of the one or more springs within the scope of the present invention.

In the preferred, exemplary embodiment depicted in FIGS. 1 and 3A, the spring mechanism includes two springs 70A and 70B that are preferably mirror images of each other. The springs are preferably metallic, and the springs deflect upon insertion into the bracket door and provide spring forces when interacting with the bracket door and the bracket body. In a preferred aspect, these springs each provide three different forces: a force required to begin opening the bracket door, a force required to begin closing the bracket door, and a force occurring roughly halfway between the open position and the closed position that is required to propel the door to either of the two positions.

Figure 4A:
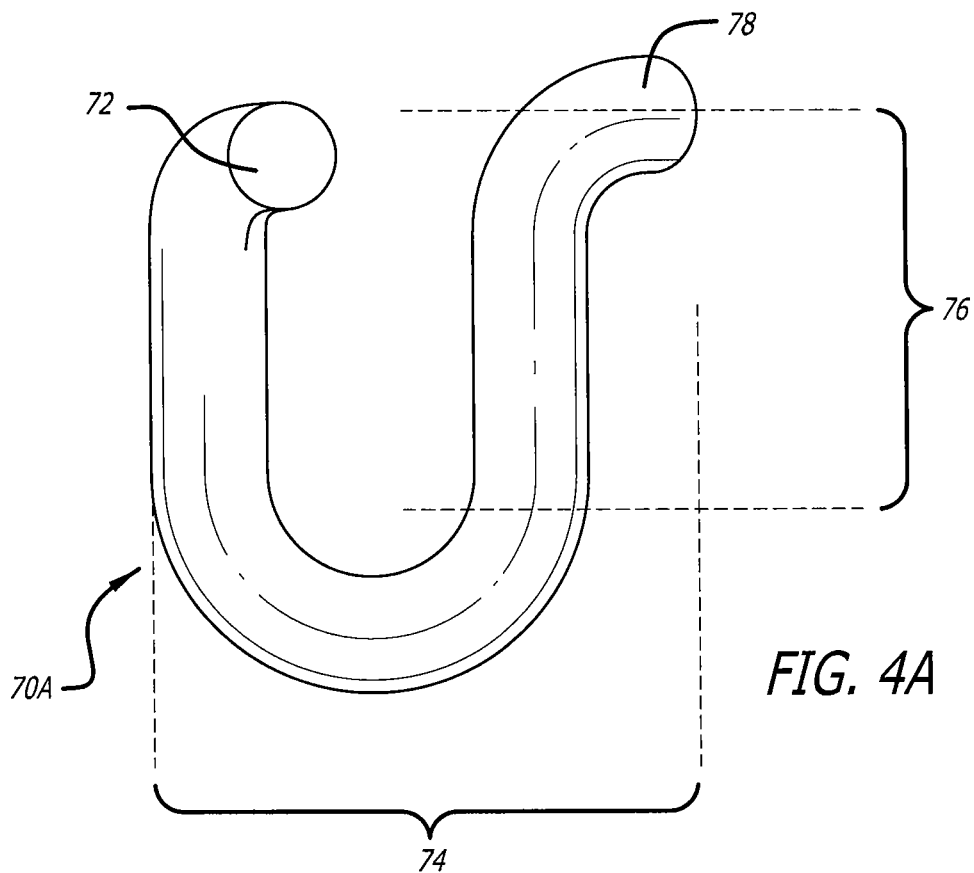
FIG. 4A is a perspective view of a spring that contacts the bracket body and the bracket door illustrated in FIG. 1.
Figure 4B:
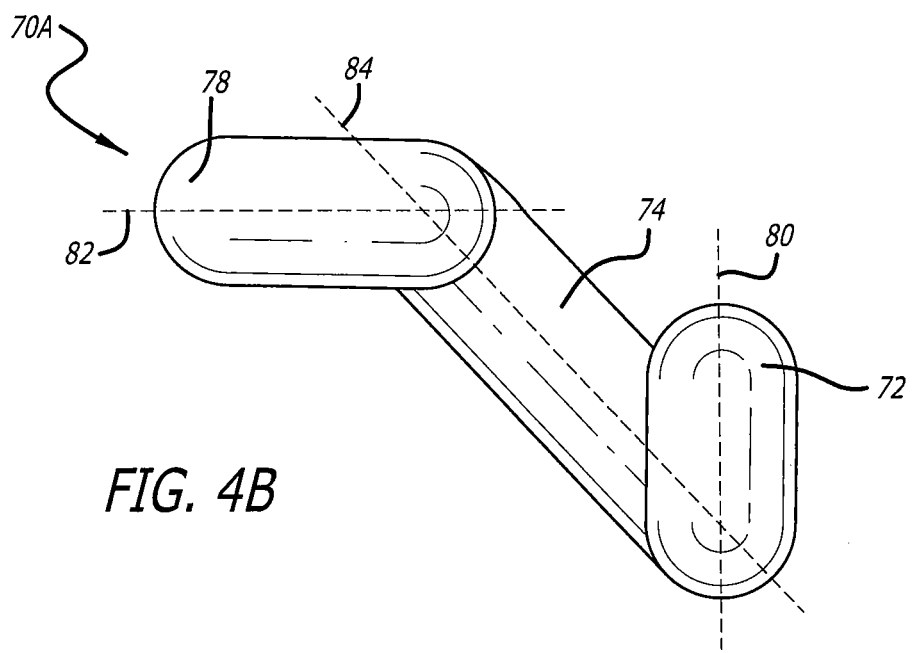
FIG. 4B is a side elevational view of the spring of FIG. 4A.

FIGS. 4A and 4B illustrate a preferred geometry or configuration of each spring, although only one of the two springs (70A) is illustrated for simplicity. Each spring has a first end 72, an intermediate segment 74 including a spring portion 76, and a second end 78. The intermediate segment is preferably shaped to maximize the running length of the spring and distribute stresses caused by movement of the bracket door, for example, by having a U-shaped configuration of one or more spring coils as illustrated in FIG. 4A. The first end of each spring is sized to engage or contact a cavity (for example, cavities 60 or 64) on the bottom side of the bracket door, and the second end of each spring is sized to engage or contact a depression in a recess (for example, recesses 30 or 34) on the bracket body. The intermediate segment of each spring is sized to fit, engage, or contact a trailing groove (for example, groove 62 or 66) on the bottom side of the bracket door and wrap or fit around a spring recess (for example, spring recess 68) along an external or internal surface of the bracket door. For example, as shown in FIG. 3B, the intermediate segment of each spring may wrap around the spring recess along an external surface of the bracket door.

Preferably, the springs are round wire springs, thus providing for ease, cost-savings, and tighter tolerances in manufacturing. The second ends of each spring are preferably formed into a smooth round, or semi-round, surface during manufacture, allowing these spring ends to glide along the recesses in the bracket groove to operate the bracket door.

According to a preferred aspect of the exemplary embodiment depicted in FIG. 1, both springs are mirror images of each other and thus operate with approximately identical opposing forces during opening or closing of the bracket door, thereby preventing the bracket door from binding. According to another preferred aspect, both springs can be used for self-ligating orthodontic brackets regardless of bracket prescription and tip angle without the need for individual springs to be dedicatedly designed for each bracket's prescription, thus allowing for ease of manufacture and economy of scale (i.e. cost-effectiveness). Preferably, the one or more springs, the one or more cavities on the bracket door, and the one or more depressions on the bracket body are individually oriented different distances from the bracket slot to accommodate for the bracket's tip angle, thus enabling the use of approximately identical springs for each bracket regardless of prescription. In this way, the preferred embodiment is a significant improvement over the prior art, since it allows for economy of scale in the production of springs without requiring individually different springs to be manufactured for each change in bracket prescription or tip angle. Additionally, the positioning of the one or more depressions on the bracket body such that their center lines (e.g. 42A and 42B in FIG. 2) are perpendicular to the bracket's tip angle provides for an even transition of the bracket door between the open and closed position with approximately identical forces imposed on and by both springs, regardless of the bracket's tip angle and irrespective of whether the one or more depressions are positioned on the sides of the bracket body or in the bracket groove.

The present invention's use of mirror image springs in the preferred embodiments described herein is significantly advantageous over prior self-ligating brackets since these springs can be used universally for all bracket prescriptions, regardless of tip angle, torque, and in-out. Orthodontic bracket prescriptions are numerous and may include various tip angles and torques that change depending on whether the bracket prescription is MBT, Roth, Andrews, Hilgers, Ricketts, or any other prescription, and depending on whether the bracket is applied to centrals, laterals, cuspids, bicuspids, incisors, or any other maxillary or mandibular teeth. The preferred embodiments' use of mirror image springs 70A and 70B therefore provides significant benefits of cost-effectiveness and economy of scale since these springs can be used for a plurality of bracket prescriptions without requiring the configurations of the springs to be uniquely designed for each tooth and for each change in bracket tip angle or torque.

It is important to note that, although these mirror image springs have been described above as being retained by the bracket door, the benefits provided by the use of mirror image springs apply equally in alternative embodiments where the springs are retained by the bracket body. In this way, the springs may be used universally for all bracket prescriptions, regardless of tip angle and torque, no matter whether the springs are borne by the bracket door or the bracket body.

According to a preferred aspect, the one or more springs are oriented such that their sections occupy three different planes. Specifically, the first end of each spring is aligned along a first plane, hereinafter referred to as a spring locking plane 80. The second end of each spring is aligned along a second plane different from the first plane and perpendicular to the tip angle of the bracket body, hereinafter referred to as the spring action plane 82. Finally, the intermediate segment of each spring is sized to have a maximum running length along a third plane different from, and angled with respect to, both the first plane and the second plane, hereinafter referred to as the spring body plane 84. In the exemplary embodiment depicted in FIG. 4B, the spring action plane is orthogonal to the spring locking plane, and the spring body plane is angled 45 degrees with respect to both the spring locking plane and the spring body plane. However, other angular relationships between all three planes are possible; for example, the spring action plane may be parallel to the spring locking plane, and the spring body plane may be acutely angled at other degrees with respect to both the spring action plane and the spring locking plane. The unique positioning of the multiple sections of each spring along these planes preferably allows each section to expand and deflect independently of each other, allows the spring mechanism to be securely retained by both the bracket door and the bracket body without ease of disassembly, and enables the bracket door to operate, all as described with reference to FIGS. 5-10 hereafter.

Figure 5:
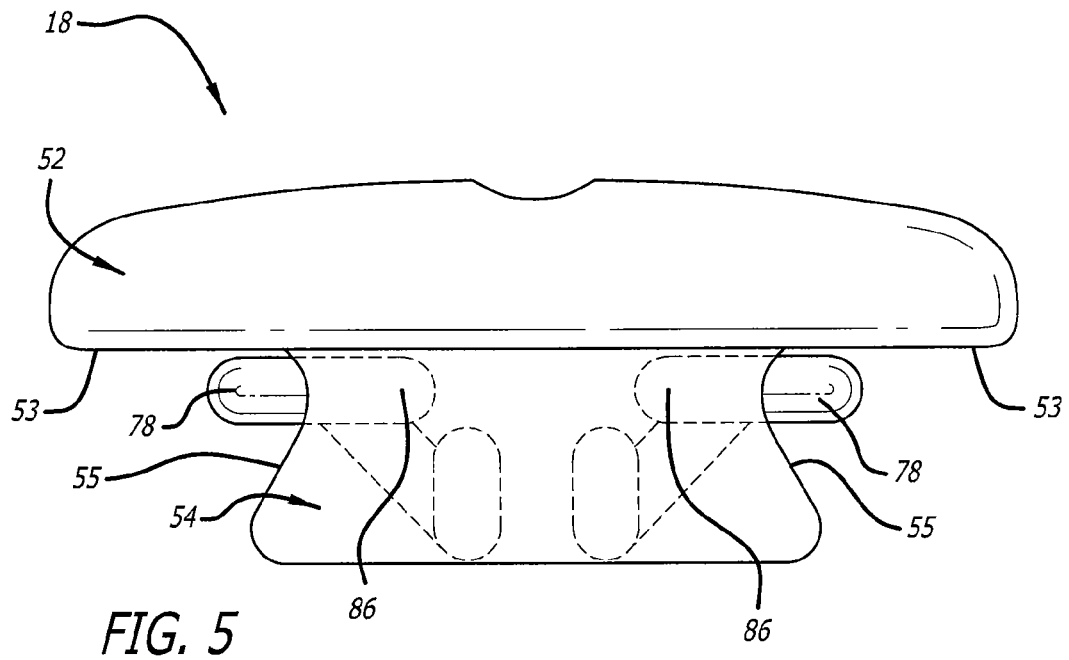
FIG. 5 is a gingival side view of the bracket door illustrating the positioning of the springs in relation to the bracket door.
Figure 6:
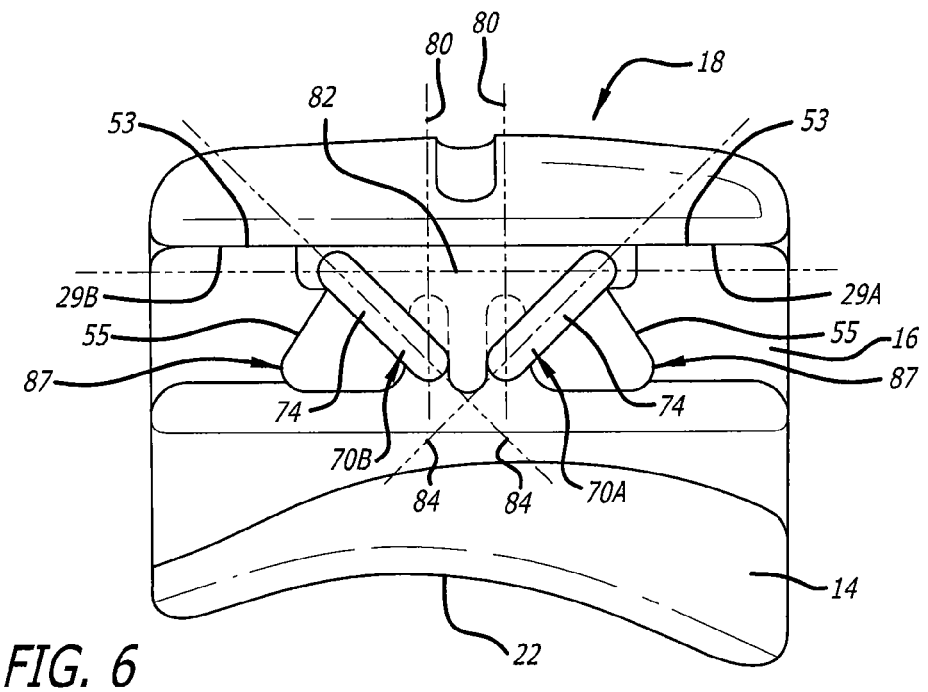
FIG. 6 is an occlusal side view of the self-ligating orthodontic bracket where the springs are properly positioned on the bracket door and the bracket door engages with the bracket body.

FIGS. 5 and 6 illustrate the positioning of the spring mechanism with respect to the bracket door embodied in FIGS. 3A and 3B. According to a preferred aspect, the first end of each spring engages or contacts the cavities on the bottom side of the door base of the bracket door along the spring locking plane, leaving the second end of each spring free to move along the spring action plane in engagement with the recesses adjacent to the bracket groove on the bracket body. According to another preferred aspect, the bracket door includes relief areas or cavities 86 (also shown in FIG. 3B) that provide space in which the spring portion 76 can deflect while the bracket door is installed to, or moved along, the bracket body. These relief areas preferably have rounded edges sized to receive the round wire springs. They are preferably hidden from view and not exposed on the bracket's external surface, and they allow for maximal deflection of the springs along the spring action plane when the bracket door is installed to the bracket body.

As emphasized in FIGS. 5 and 6, the door base of the bracket door is preferably shaped in the form of a dovetail. The dovetail shape maximizes the total area in which the one or more springs can be placed or inserted into the bracket door. Moreover, the dovetail shape allows for the maximum running length of each spring to help distribute stresses and thereby improve the stress flow caused by movement of the door. Moreover, the dovetail shaped bracket door provides for increased cross-sectional thickness that is critical to the strength of the bracket and improves the strength of the bracket door. Furthermore, the cross-sectional thickness of the bracket door in combination with the fact that the bracket door preferably covers the full expanse of the bracket slot allows for stresses imposed by movement of the archwire during treatment to be translated along the entire door's width to the bracket door's dovetail, further improving the strength of the bracket. Preferably, the bracket door also has a curved shape that reduces stress concentrations imposed by movement of the archwire and allows for ease of manufacture during injection molding.

The dovetail shape further helps to retain the spring mechanism in the bracket door by allowing for the maximum running length of the one or more springs. When the intermediate segments of each spring are wrapped around a surface of the bracket door along the spring body plane, for example, within the curved spring recesses 68 as shown in FIGS. 3B and 6, the first end of each spring helps to prevent the spring mechanism from disassembling from the bracket door. In alternative embodiments, for example, where the spring recess curves around an internal surface of the bracket door, the intermediate segment of the one or more springs helps to prevent the spring mechanism from disassembling from the bracket door. As a result, the first end or intermediate segment of each spring may assist in preventing the spring mechanism from disassembling from the bracket door and allows each spring to securely lock into the bracket door without the need for additives or adhesives. Although slight deformation of the intermediate segment of each spring along the spring body plane may occur, the intermediate segments of each spring are preferably sized to have a large curving bend that allows for easy installation of the spring mechanism without causing any permanent deformation to the springs during assembly.

Furthermore, the bracket groove is preferably shaped to slidingly receive the door base of the bracket door. The opposing side slots 87 of the bracket groove are preferably curved to complementarily receive the dovetail-shaped door base of the bracket door. Moreover, the opposing side slots 87 guide and support the bracket door, particularly the opposing side edges 55 of the door base, as it moves along a single axis away from and towards the bracket slot between the opened and closed positions. Additionally, the mesial surface 29A and distal surface 29B of the bracket body support the opposing side edges 53 of the door head as the bracket door moves between the opened and closed positions. The bracket body thus prevents the bracket door from moving along any other plane of motion, thereby preventing binding and reducing stress risers when the bracket door undergoes stress from the archwire.

Furthermore, when the bracket door with the spring mechanism is pressed along the tapered sides 50 into the bracket groove of the bracket body during installation of the bracket door, the spring portion 76 of each spring deflects along the plane of spring action, preferably elastically and alternatively plastically, until the second ends of each spring slide into their respective depressions (38 and 46), thereby retaining the bracket door in the bracket body without the need for adhesives or additives. In addition, the springs form a surface-to-surface contact with the bracket body that does not allow the springs to deflect when trying to move the bracket door back past the open position in attempt to disassemble the bracket. This configuration thus requires more force to disassemble the bracket door from the bracket body due to the geometry of the bracket groove and the positioning of the spring mechanism, therefore allowing for ease of assembly and relatively difficult disassembly without requiring crimping, bending, coining, fastening, gluing, or other similar assembly methods which were conventionally used in prior self-ligating brackets.

Therefore, the preferred embodiment implements a double locking mechanism, where the first ends of the springs lock into the bracket door, and the second ends of the springs lock into the bracket body, without the need for additives, adhesives, crimping, bending, coining, fastening, or gluing the bracket door to the bracket body. This mechanism thus only allows for disassembly of the bracket door through deflection of the springs along the plane of spring action, which is difficult to achieve due to the bracket's imposed physical barrier on the spring mechanism. Therefore, the bracket door can only be disassembled from the bracket by significant deformation of the one or more springs. Additionally, the tight engagement of the spring mechanism to the bracket body and the bracket door preferably results in no hollows or room, and thus minimal empty space, for plaque or calcification to grow.

Figure 7:
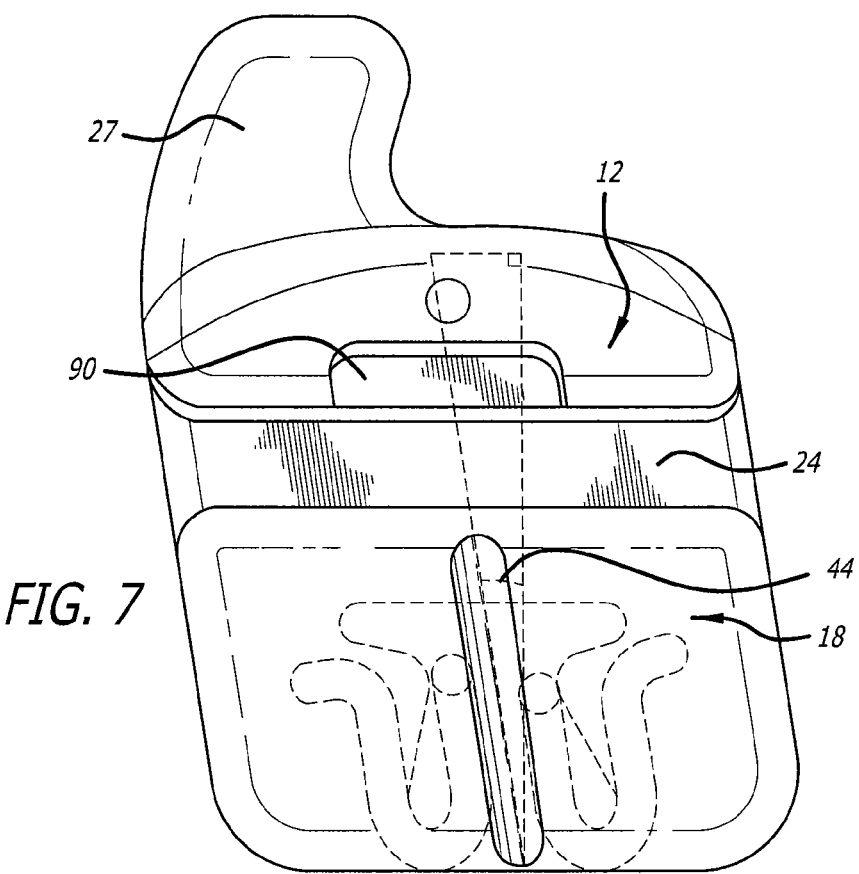
FIG. 7 is a top plan view of the self-ligating orthodontic bracket showing the door in the open position such that the bracket slot is exposed to place or remove an archwire.
Figure 8:
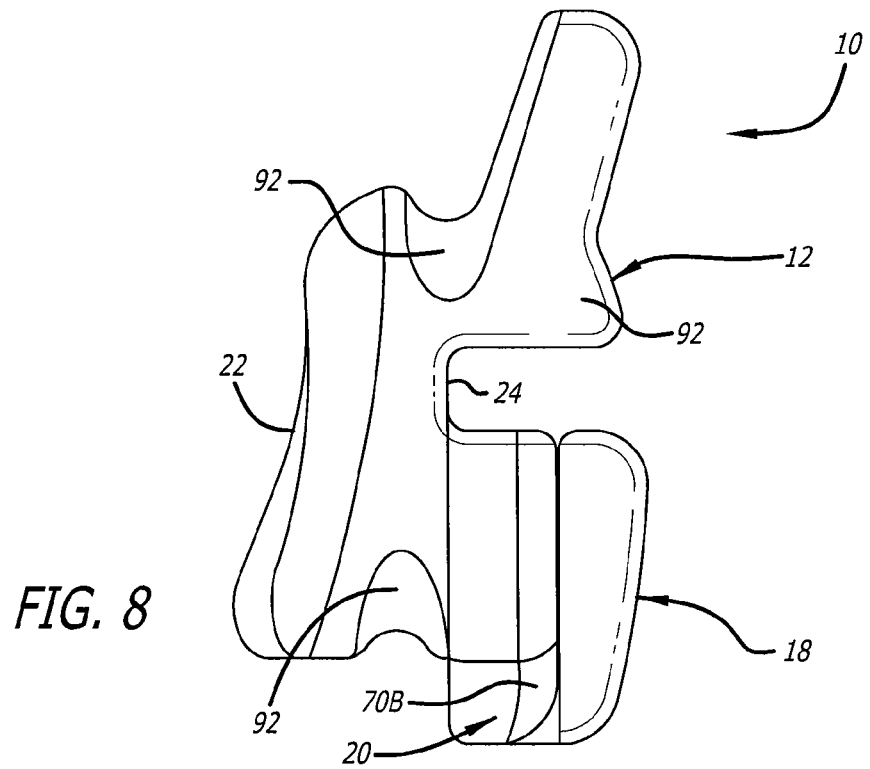
FIG. 8 is a mesiodistal side elevational view of the self-ligating orthodontic bracket depicted in FIG. 7 showing the door in the open position.
Figure 9:
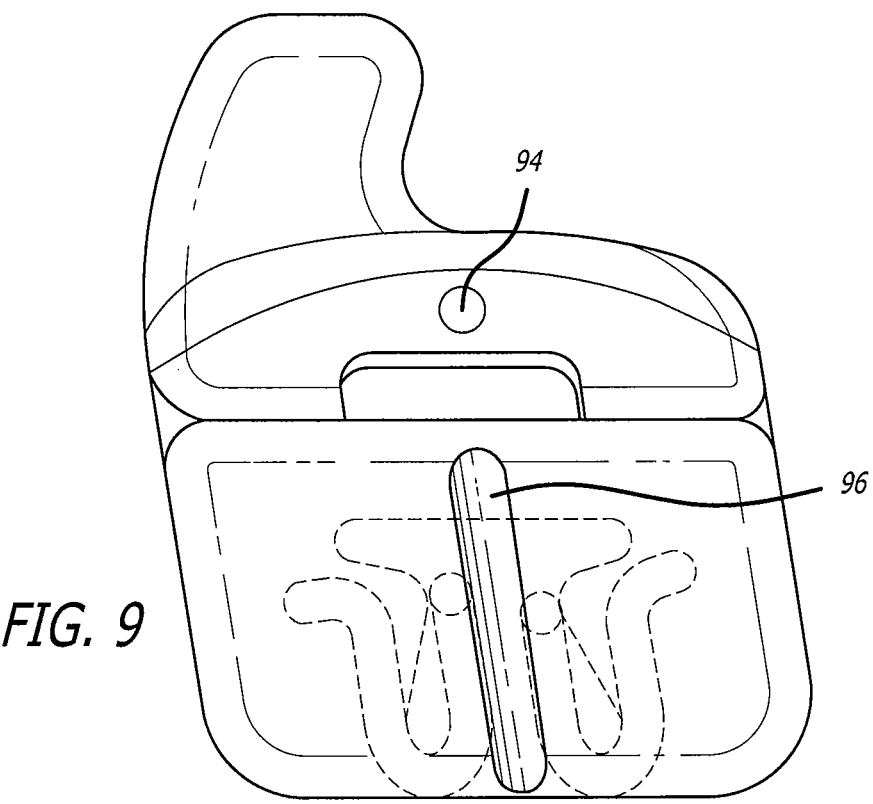
FIG. 9 is a top plan view of the self-ligating orthodontic bracket showing the door in the closed position such that the bracket door encloses the bracket slot to securely retain an archwire.
Figure 10:
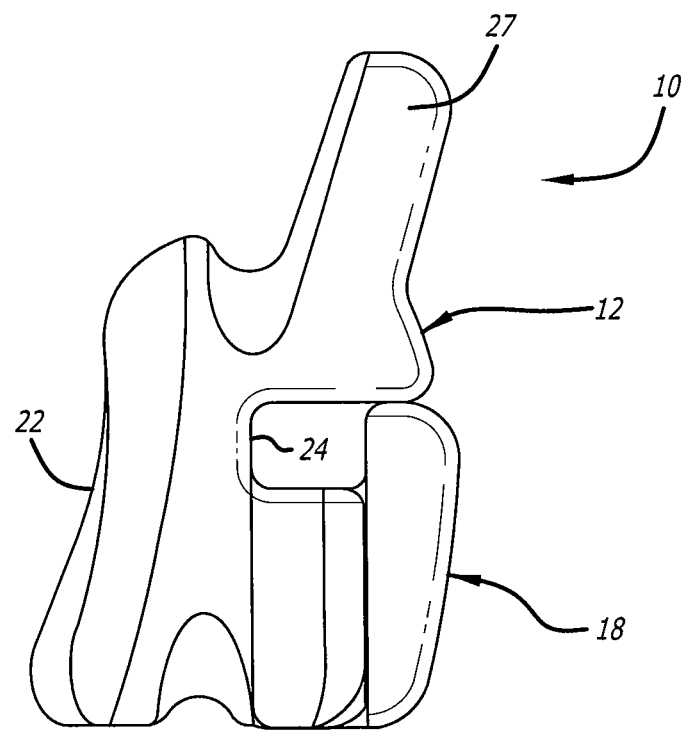
FIG. 10 is a mesiodistal side elevational view of the self-ligating orthodontic bracket depicted in FIG. 9 showing the door in the closed position.
Figure 11A:
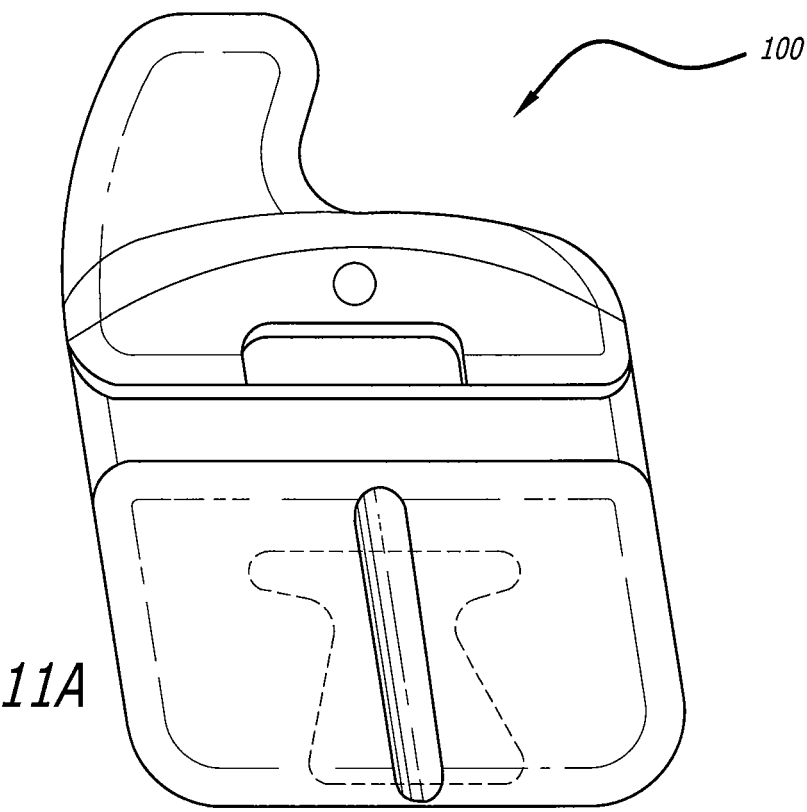
FIG. 11A is a top plan view of an exemplary self-ligating orthodontic bracket according to the preferred embodiment depicted in FIG. 1 with the door in the open position.
Figure 11B:
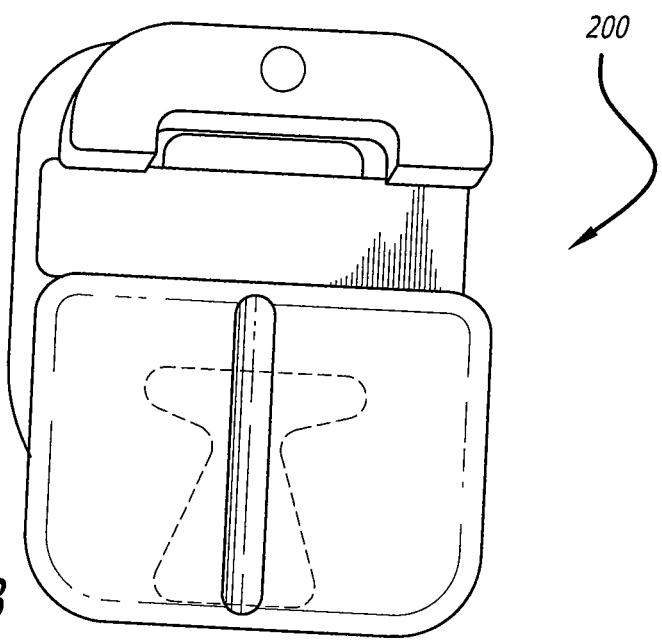
FIG. 11B is a perspective view of another exemplary self-ligating orthodontic bracket according to the preferred embodiment depicted in FIG. 1 with the door in the open position.
Figure 12A:
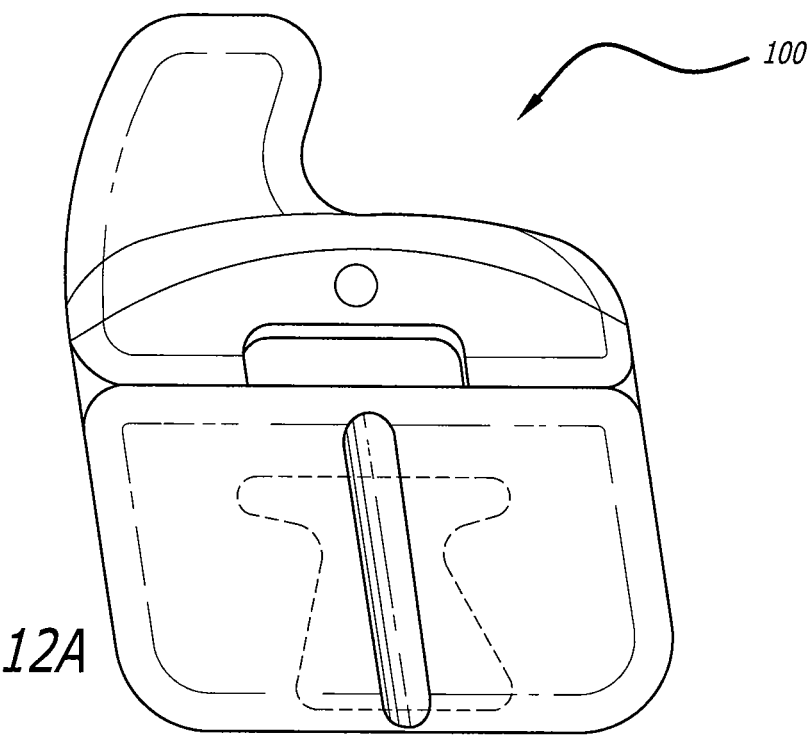
FIG. 12A is a top plan view of the self-ligating orthodontic bracket shown in FIG. 11A showing the door in the closed position.
Figure 12B:
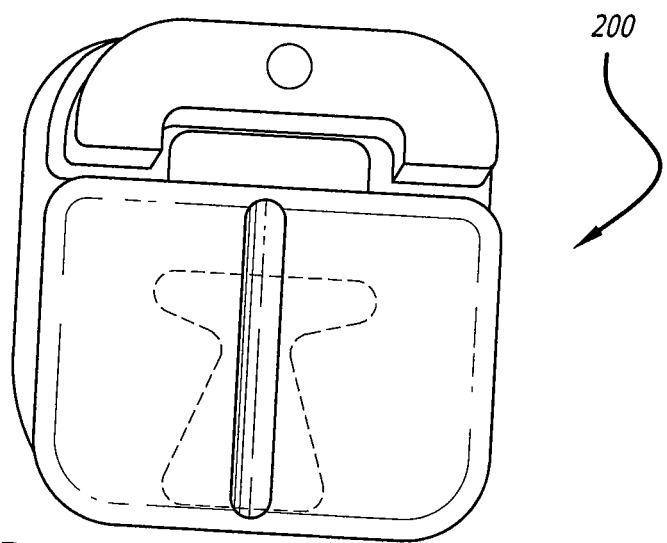
FIG. 12B is a perspective view of the self-ligating orthodontic bracket shown in FIG. 11B showing the door in the closed position.
Figure 13A:
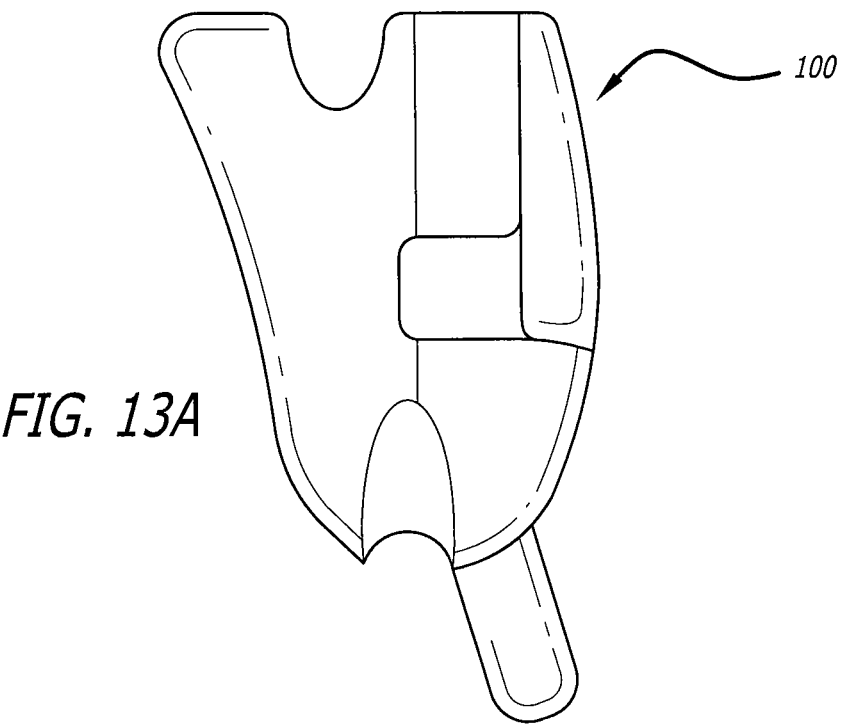
FIG. 13A is a mesiodistal side elevational view of the self-ligating orthodontic bracket depicted in FIG. 12A.
Figure 13B:
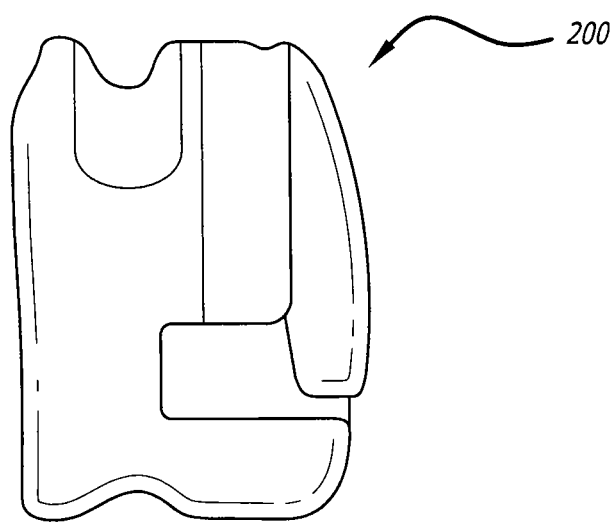
FIG. 13B is a mesiodistal side elevational view of the self-ligating orthodontic bracket depicted in FIG. 12B.

FIGS. 7-10 illustrate the above-described preferred embodiment of the self-ligating bracket after the bracket door has been successfully assembled onto the bracket body. Particularly, FIGS. 7-8 depict the bracket door in the open position, while FIGS. 9-10 depict the bracket door in the closed position. When the bracket door is open, the bracket slot is exposed, allowing a user to remove or place an archwire in the bracket slot. When the bracket door is closed, the bracket door fully encloses the archwire in the bracket slot, thereby allowing the bracket to passively express its prescription. Alternatively, the spring mechanism may include an additional spring that is adapted to contact the archwire during movement, such as described below with reference to FIGS. 17-20, thereby allowing the bracket to fully or actively express its prescription.

Movement of the bracket door along the bracket groove is relatively straightforward. According to a preferred aspect, both recesses on either side of the bracket groove include depressions which taper towards each other until a midpoint 88 (see FIG. 2). These midpoints or tapered angles define the position where the bracket door smoothly transitions and propels from the open position to the closed position, and vice-versa. For example, when the bracket door is in the open position, the second ends of each spring engage the mesial first depression and the distal first depression, respectively. As the bracket door moves along the bracket groove toward the bracket slot, the second ends and spring portion 76 of each spring elastically or plastically deflect within relief areas 86 towards the center of the bracket groove in a direction perpendicular to the bracket's tip angle 44 as the depressions taper off towards their respective midpoints. Once the second ends of each spring reach their respective midpoints, the tension caused by the deflection of the springs is allowed to release, translating into a linear force that propels or biases the bracket door along the bracket groove to the closed position. A similar procedure takes place when the bracket door is moved from the closed position to the open position. Due to the approximately identical lengths of each spring's portion 76, both springs respond with approximately identical forces regardless of the bracket's tip angle and prevent biasing of the door towards either side of the bracket body, thus preventing binding of the bracket door.

Various other bracket features may also be included as preferred aspects. According to one preferred aspect, the top side of the bracket body includes a tool depression 90 (see FIG. 7) positioned adjacent to the bracket slot which is preferably sized to accept a torqueing mechanism that can be used to pry open the bracket door, such as a flathead screwdriver. According to another preferred aspect, the bracket door may be opened without a tool. According to another preferred aspect, the bracket body includes curved tie wings having grooves 92 (see FIG. 8) on both the occlusal side and the gingival side of the bracket body for possible use of optional ligatures. These curved tie wings are preferably made using a rounded cut, allowing for improved fit and strength and better retention of elastomeric bands.

According to another preferred aspect, the top side of the bracket body includes an area 94 and a groove 96 (see FIG. 9) on which visual orthodontic references may be applied, such as color-coded markings, thus allowing the bracket to provide a doctor with distinct visual cues that for instance describe the vertical and archwire axis of the bracket. According to a further preferred aspect, the head of the bracket door is sized to a cross-sectional thickness allowing for improved strength and durability of the bracket. According to another preferred aspect, the depressions on the bracket body have curvatures that are sized for bracket strength and conventional ceramic or metallic bracket injection molding and are sized to perfectly mate with the round wire springs, thereby allowing for improved gliding action of the bracket door with less chance of binding.

FIGS. 11A-13B illustrate exemplary embodiments of the above-described self-ligating bracket in both the open position and the closed position. The illustrations here depict two examples of self-ligating brackets for two different teeth, specifically an upper cuspid bracket 100 such as a U3R bracket for placement on a maxillary or upper tooth (see FIGS. 11A, 12A, and 13A), and a lower anterior bracket 200 such as a L12 bracket for placement on a mandibular or lower tooth (see FIGS. 11B, 12B, and 13B). Although only two examples for two different teeth are here illustrated, it is to be understood that the self-ligating orthodontic bracket may be designed for placement on any maxillary and mandibular tooth.

Figure 14:
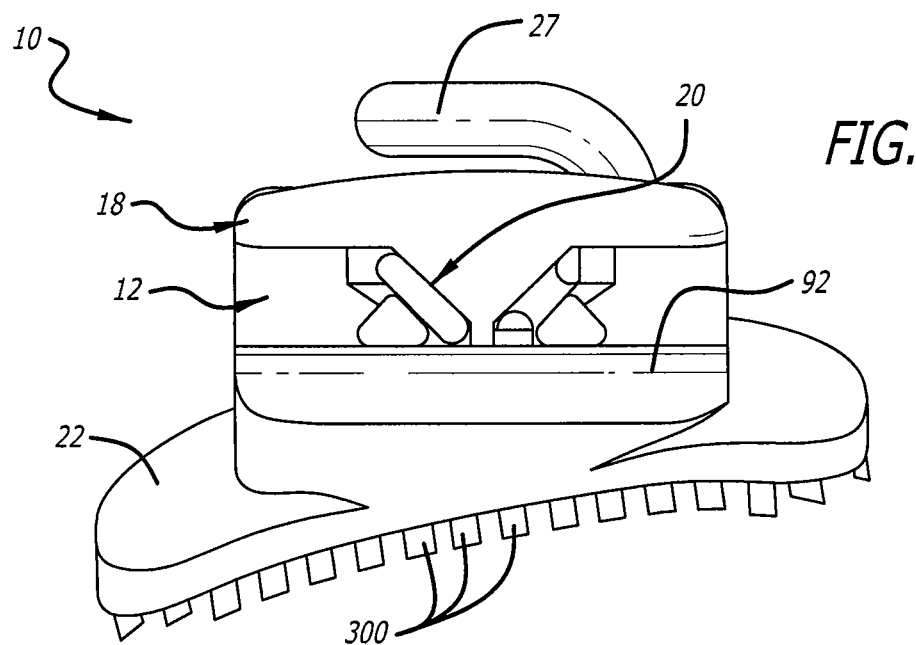
FIG. 14 is an occlusal side view of a self-ligating orthodontic bracket for a molar tooth according to an alternative aspect of the preferred embodiment depicted in FIG. 1.
Figure 15:
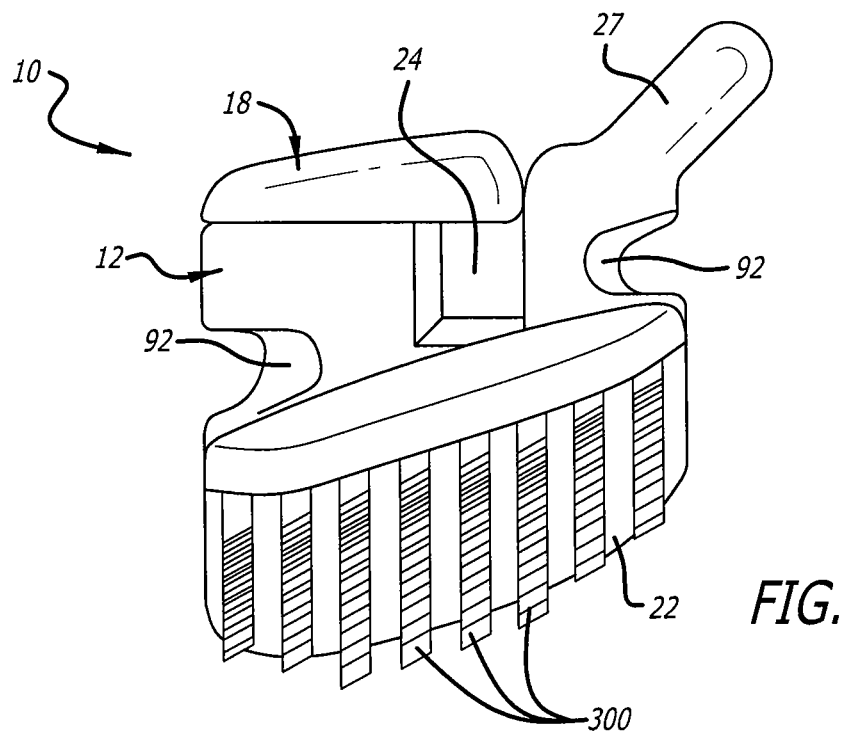
FIG. 15 is a mesiodistal side elevational view of the self-ligating orthodontic bracket depicted in FIG. 14.
Figure 16:
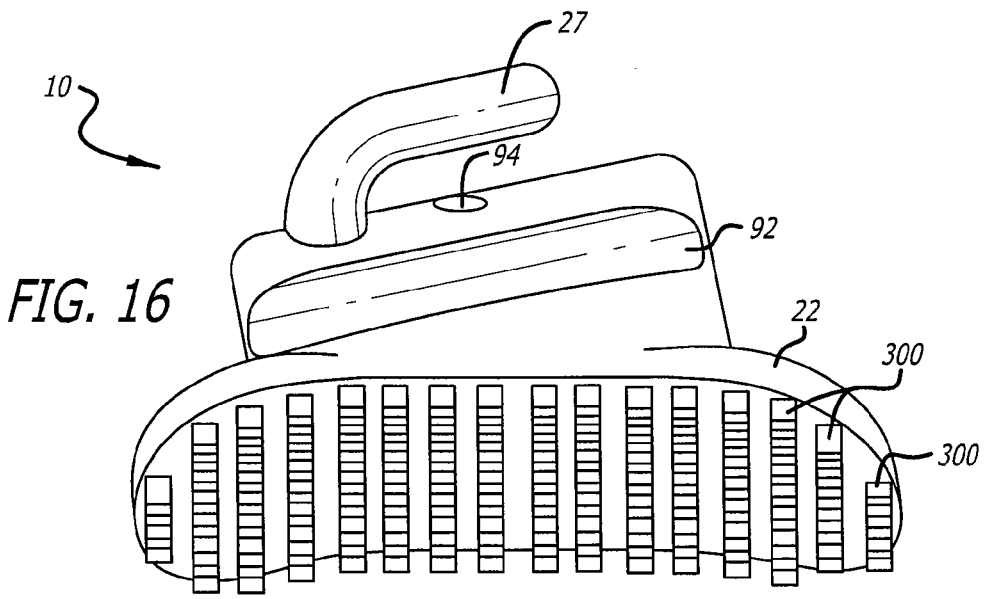
FIG. 16 is a gingival side view of the self-ligating orthodontic bracket depicted in FIG. 14.

FIGS. 14-16 illustrate an alternative, preferred aspect of the preferred embodiment depicted in FIGS. 1-13B as applied on a molar tooth. Specifically, FIGS. 14-16 illustrate the self-ligating orthodontic bracket 10 described above, including bracket body 12, dovetail-shaped bracket door 18, and spring mechanism 20 of one or more springs that propels the bracket between the open and closed positions. In this aspect, however, base 22 is dual-compound contoured and includes pylons 300 for bonding the base to a surface of a molar tooth. The one or more springs in this aspect are identical to those used in the spring mechanism illustrated in FIGS. 1-13B, and thus operate with approximately identical opposing forces during opening or closing of the bracket door. In this way, the self-ligating bracket 10 is a significant improvement over the prior art, since it allows for economy of scale in the production of springs without requiring individually different springs to be manufactured for each change in bracket prescription or tip angle.

According to a preferred aspect, the pylons on the base allow for maximal bonding surface area and improved bond strength. Additionally, the base is preferably micro-etched to provide greater bond strength. Furthermore, it should be noted that although pylons are expressly referenced in the Figures, other bonding systems may be used. For instance, a mesh base may be used, or a smooth base with small shards of ceramic. These bonding systems may be applied to any maxillary or mandibular tooth.

Various other preferred aspects for the self-ligating bracket are provided. In one preferred aspect, the bracket door and bracket body may be metallic or ceramic, while the spring mechanism is metallic. In another preferred aspect, the bracket in FIGS. 14-16 may include a hook 27 that is shaped to facilitate attachment of an elastomeric, such as a ligature, onto the hook, without coming into contact with the gingiva. The shape of the hook may vary depending on the material used for the self-ligating bracket to provide increased strength for the bracket. In a further preferred aspect, the bracket slot 24 has a fluted inlet to facilitate insertion of an archwire into the bracket slot while the bracket door is in the closed position. In an additional preferred aspect, the self-ligating bracket includes curved tie wing grooves 92 underneath the tie wings on the occlusal side and the gingival side of the bracket body to allow for the use of optional ligatures or other elastomerics. In a further preferred aspect, the self-ligating bracket may include an area 94 or groove 96 on which visual orthodontic references may be applied, such as color-coded markings, thus allowing the bracket to provide a doctor with distinct visual cues that for instance describe the vertical and archwire axis of the bracket.

In yet another preferred aspect, when the bracket door is closed, the bracket door fully encloses the archwire in the bracket slot, thereby allowing the bracket to passively express its prescription. In another preferred aspect, the bracket door may include an additional spring that is adapted to contact the archwire during movement, such as described with reference to FIGS. 17-20 below, thereby allowing the bracket to fully or actively express its prescription.

FIGS. 17-20 illustrate an alternative preferred aspect of the preferred embodiment of the self-ligating orthodontic bracket described and depicted above with reference to FIGS. 1-16, including an additional spring to actively press against the archwire. Specifically, FIGS. 17-20 illustrate self-ligating orthodontic bracket 10 including bracket body 12, dovetail-shaped bracket door 18, and one or more springs that engage one or more depressions on the bracket body, bias or propel the bracket between the open and closed positions, and prevent disassembly of the bracket door from the bracket body. However, in this preferred aspect, the first end 72 and the second end 78 of the one or more springs (70A, 70B) are aligned on parallel planes instead of orthogonal planes (which are referenced in FIG. 4B as spring locking plane 80 and spring action plane 82, respectively). Additionally, the first end 72 of each spring is positioned on and retained by ledges 302 (see FIGS. 18 and 19) on either side of the door base 54, which replace the mesial and distal cavities 60 and 64 illustrated in FIG. 3A.

According to a preferred aspect of the bracket depicted in FIGS. 17-20, the spring mechanism 20 includes two springs that are mirror images of each other and thus operate with approximately identical opposing forces during opening or closing of the bracket door, thereby preventing the bracket door from binding. According to a preferred aspect, both springs can be used for self-ligating orthodontic brackets regardless of bracket prescription and tip angle without the need for individual springs to be dedicatedly designed for each bracket's prescription, thus allowing for ease of manufacture and economy of scale (i.e. cost-effectiveness). In this way, the preferred embodiment is a significant improvement over the prior art, since it allows for economy of scale in the production of springs without requiring individually different springs to be manufactured for each change in bracket prescription or tip angle.

The benefits of cost-effectiveness and economy of scale brought by the use of mirror image springs are significantly advantageous over prior self-ligating brackets since these springs can be used universally for all bracket prescriptions, regardless of tip angle and torque. It is important to note that, although these mirror image springs have been described above as being retained by the bracket door, the benefits provided by the use of mirror image springs apply equally in embodiments where the springs are retained by the bracket body. In this way, the springs may be used universally for all bracket prescriptions, regardless of tip angle and torque, no matter whether the springs are borne by the bracket door or the bracket body.

Figure 17:
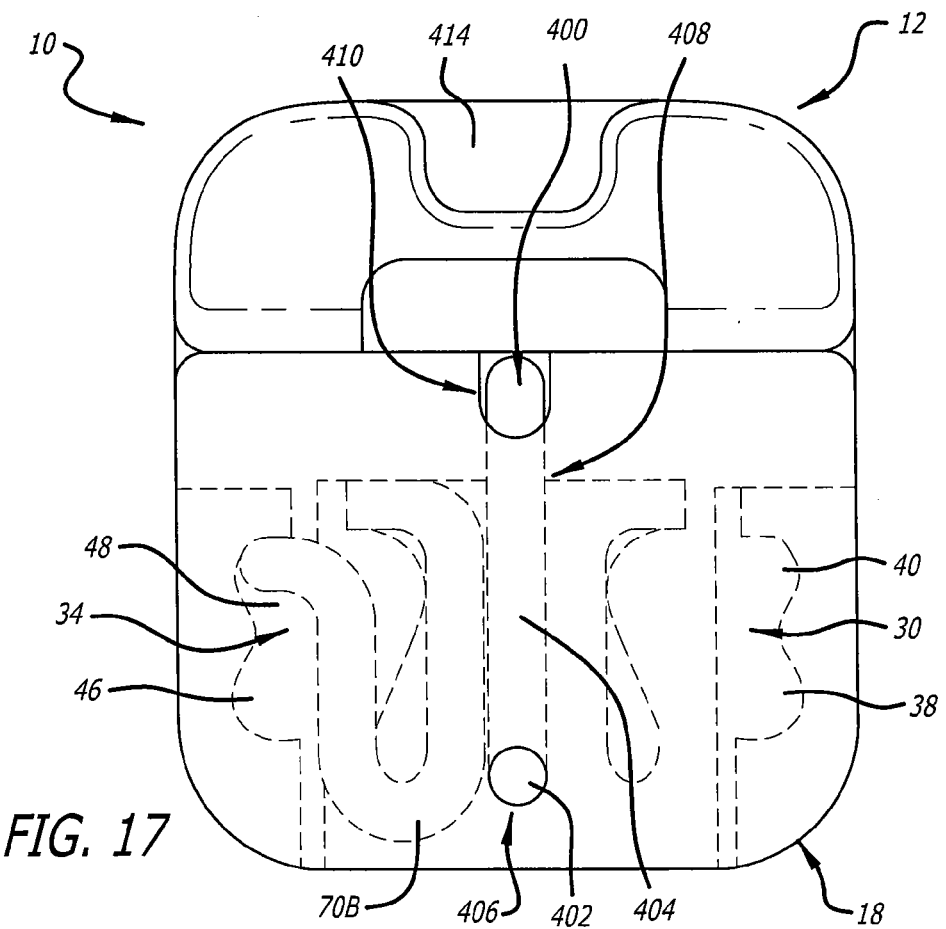
FIG. 17 is a top plan view of a self-ligating orthodontic bracket including a bracket body, a bracket door, and one or more springs according to the preferred embodiment depicted in FIG. 1, and having an additional active spring member retained by the bracket door.

Referring to FIG. 17, in this preferred aspect, there are provided one or more additional, active spring members 400 that are borne by the bracket door and positioned to contact or press against the archwire 26. Although a single active spring member 400 is depicted in the Figures as aligning with the center of the self-ligating bracket, it should be noted that multiple active spring members 400 may be positioned at a plurality of locations anywhere along the width of the bracket.

The one or more active spring members preferably have a first portion or retaining portion 402, and a second portion or contacting portion 404. Preferably, the retaining portion 402 is insertable into and borne by the bracket door. Alternatively, the active spring member 400 is a tang integrally borne by and extending from the bracket door as a single component. The contacting portion 404 is configured to contact the archwire in the bracket slot when the bracket door is in the closed position and to progressively apply a force against the archwire that is directly proportional to the archwire's size. Complementing the one or more active spring members are one or more active spring cavities 406 and one or more active spring channels 408 located on the bracket door.

Figure 18:
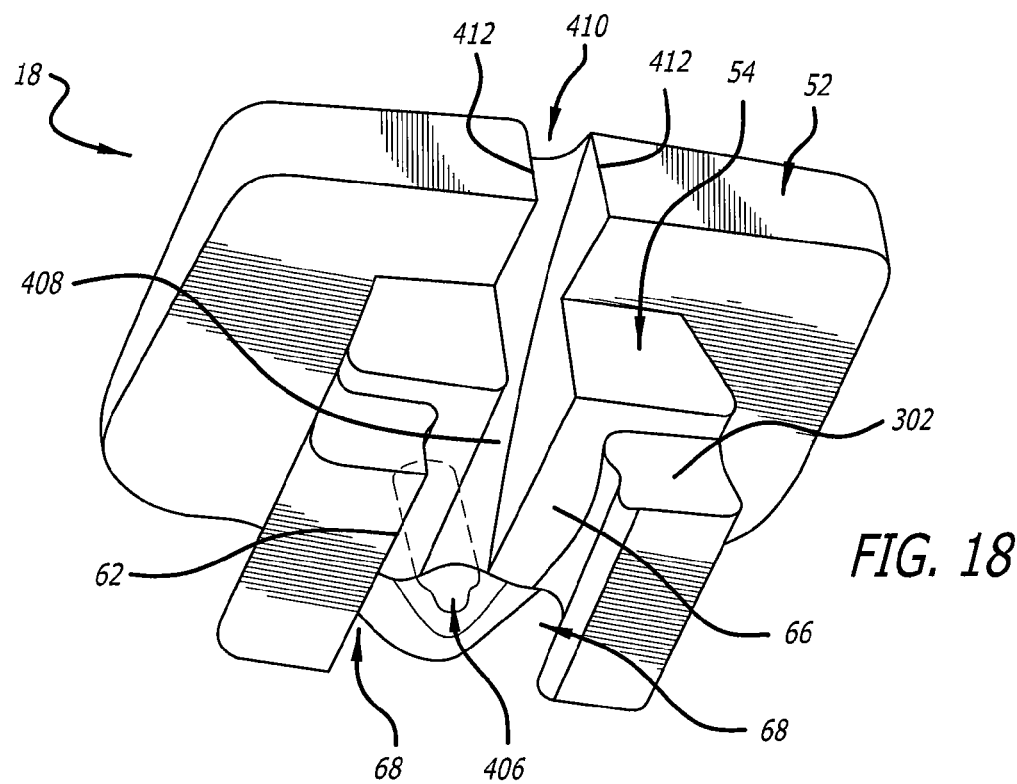
FIG. 18 is a perspective view of the lingual side of the bracket door depicted in the self-ligating orthodontic bracket illustrated in FIG. 17.
Figure 19:
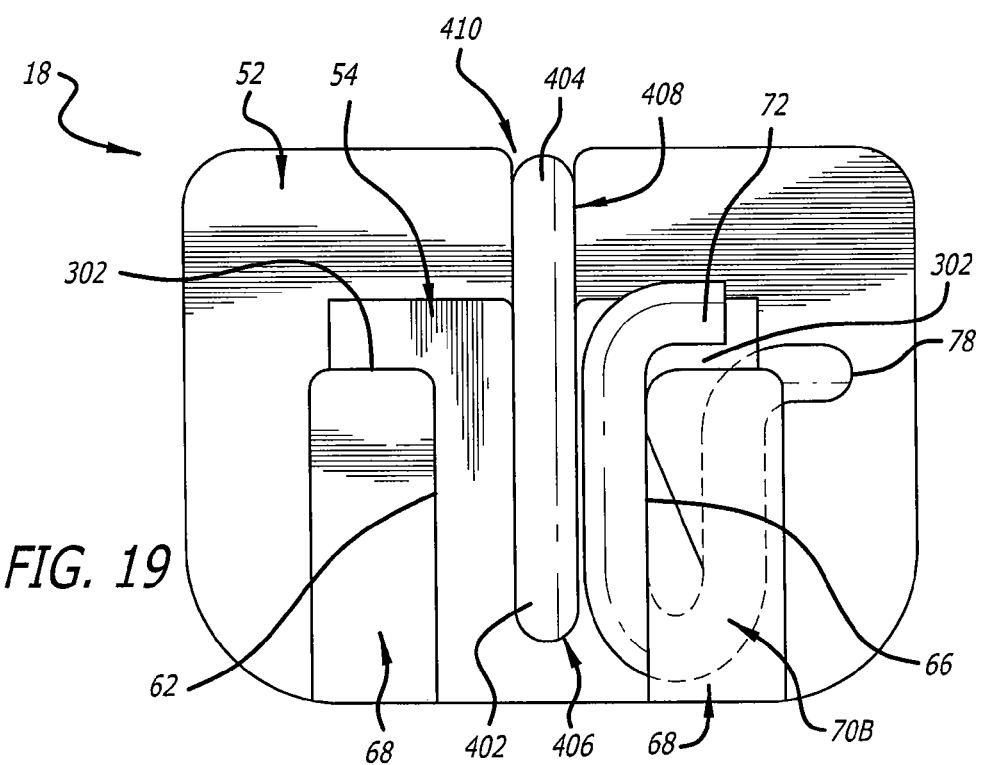
FIG. 19 is a lingual side view of the bracket door depicted in FIG. 18 illustrating the active spring member.

The configuration of the one or more active spring cavities and active spring channels allow the bracket door to fully retain the one or more active spring members. In the preferred aspect described with reference to FIGS. 17-18, an active spring cavity 406 is centrally located on the bottom or lingual side of the door base 54 of the bracket door and is sized to receive and retain the insertable, vertically-extending retaining portion 402 of the active spring member. The active spring cavity 406 thus prevents movement of the active spring member in the vertical and horizontal directions when the bracket door is in the closed position. Alternatively, the active spring member is a tang whose retaining portion 402 is integrally fitted within the active spring cavity 406 such that the bracket door and the active spring member are formed into a single component. Additionally, the active spring channel 408 is centrally positioned to run along the lingual side of the door base 54 and door head 52 of the bracket door in the gingival direction towards the bracket slot 24 until it opens into an aperture 410 situated on the bracket door. Although FIGS. 17-18 illustrate that aperture 410 is situated on and visible from the labial side of the bracket door, aperture 410 may be situated on the lingual side of the bracket door such that it is invisible from the labial side of the bracket door. The active spring channel 408 is sized to receive the contacting portion 404 of the active spring member when it deflects from contact with the archwire. More specifically, as the size of the archwire is increased during orthodontic treatment, the contacting portion 404 of the active spring member increasingly flexes due to contact with the archwire until the maximum archwire size is used, after which the contacting portion maximally deflects and is received in the active spring channel. The active spring channel 408 further includes channel sides 412 that serve to guide the active spring member into the channel when the active spring member maximally deflects, thus preventing the active spring member from binding or deflecting away from the channel due to contact with the archwire.

According to one preferred aspect, the self-ligating bracket may include a central tie wing groove 414 (see FIG. 17) positioned on the gingival side of the bracket body that provides a purchase point for a clinician to facilitate placement of an optional elastomeric, such as a ligature. According to another preferred aspect, the self-ligating bracket includes curved tie wing grooves 92 (see FIG. 20) underneath the tie wings on the occlusal side and the gingival side of the bracket body to allow for the use of optional ligatures or other elastomerics, such as steel ligatures or power chains, either individually or multiple simultaneously. According to yet another preferred aspect, the one or more active spring members are optional and are selectively connectable to and removable from the bracket door, thereby allowing the self-ligating bracket to have both an active and passive configuration as well as economy of scale in manufacture from the use of identical bracket doors and bracket bodies in each configuration.

According to a further preferred aspect, the base 22 of the bracket body includes pylons 300 (see FIG. 20) for bonding the base to a surface of a tooth. According to a preferred aspect, the pylons on the base allow for maximal bonding surface area and improved bond strength. Additionally, the base is preferably micro-etched to provide greater bond strength. Furthermore, it should be noted that although pylons are expressly referenced, other bonding systems may be used without departing from the scope of the present invention. For instance, a mesh base may be used, or a smooth base with small shards of ceramic. These bonding systems may be applied to any maxillary or mandibular tooth.

Figure 20:
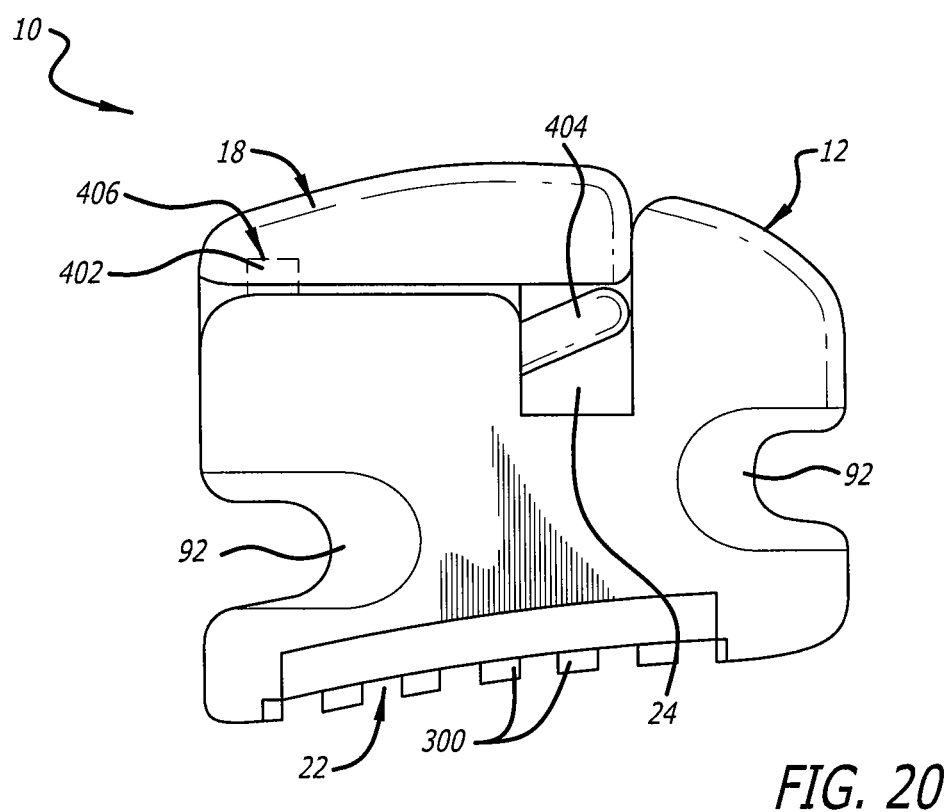
FIG. 20 is a mesiodistal side elevational view of the self-ligating orthodontic bracket depicted in FIG. 17.

As illustrated in FIG. 20, the one or more active spring members are in a resting state when the bracket slot is empty. When an archwire is inserted into the bracket slot while the bracket door is in the closed position, the one or more active spring members contact or press against the archwire. In one preferred aspect, the one or more active spring members are positioned to contact any conventionally sized archwire and apply progressively more force against the archwire in the bracket slot as the archwire size is increased, resulting in progressively greater deflection of the contacting portion 404 toward the active spring channel until a maximum conventional archwire size is used. In an alternative preferred aspect, the one or more active spring members only come into contact with the archwire at a predetermined archwire size. In this aspect, only when the archwire has the predetermined archwire size does the contacting portion press the archwire against a corner of the bracket slot opposite the one or more active spring members. In another preferred aspect, the force applied by the one or more active spring members against the archwire in the bracket slot may vary based on the temper, diameter, and geometry of the one or more active spring members.

While certain embodiments have been illustrated and described herein, those embodiments are not necessarily to be construed as advantageous over other embodiments for implementing the apparatus of the present subject matter.

Other variations and equivalents are possible and should be considered within the scope of the present subject matter.

What is claimed is:

1. An orthodontic self-ligating bracket for orthodontic treatment of maloccluded teeth, the bracket comprising:
    a bracket body having a bottom side and a top side, the bracket body including:
        a base on the bottom side of the bracket body that is contoured to attach to a surface of a tooth;
        a bracket slot on the top side of the bracket body, the bracket slot extending in a mesiodistal direction and configured to releasably retain an archwire; and
        a bracket groove on the top side of the bracket body extending towards the bracket slot and including a mesial first depression, a distal first depression, a mesial second depression, and a distal second depression;
    a bracket door having a bottom side including a mesial cavity and a distal cavity, and a top side, wherein the bracket door slidably engages the bracket groove between an open position and a closed position, wherein the bracket slot is exposed when the bracket door is in the open position to allow for placement and removal of the archwire, and wherein the bracket slot is enclosed to securely retain the archwire when the bracket door is in the closed position; and
    a mesial spring and a distal spring separate from the bracket door and configured to be borne by the bracket door and configured to propel the bracket door between the open position and the closed position wherein the bracket door is slidably movable and is propelled into the open position upon application of a force to the door such that the mesial spring slides into the mesial first depression and such that the distal spring slides into the distal first depression, and wherein the bracket door is slidably movable and is propelled into the closed position upon application of a force to the door such that the mesial spring slides into the mesial second depression and such that the distal spring slides into the distal second depression.

2. The orthodontic self-ligating bracket of claim 1, wherein the mesial spring and the distal spring each include a first end, an intermediate segment, and a second end, wherein the first end of the mesial spring engages into the mesial cavity of the bracket door and the second end of the mesial spring interacts with the mesial first and second depressions of the bracket groove, and wherein the first end of the distal spring engages into the distal cavity of the bracket door and the second end of the distal spring interacts with the distal first and second depressions of the bracket groove.

3. The orthodontic self-ligating bracket of claim 2, wherein the intermediate segments of the mesial spring and the distal spring each wrap around a surface of the bracket door.

4. The orthodontic self-ligating bracket of claim 1, further comprising:
    one or more active springs separate from the mesial and distal springs and each including a first portion and a second portion, wherein the first portion of the one or more active springs is configured to be inserted in the bracket door; and
    wherein the second portion of the one or more active springs is configured to contact the archwire in the bracket slot when the bracket door is in the closed position.

5. The orthodontic self-ligating bracket of claim 1, further comprising:
    one or more active springs separate from the mesial and distal springs and configured to contact the archwire in the bracket slot when the bracket door is in the closed position, wherein each of the one or more active springs is a tang integrally retained by the bracket door.

6. The orthodontic self-ligating bracket of claim 1, wherein the mesial and distal springs that are mirror images of each other, wherein the orthodontic self-ligating bracket has a predetermined prescription including tip angle and torque, and wherein the mesial and distal springs allow the orthodontic self-ligating bracket to operate regardless of the predetermined prescription of the bracket.

* * * * *